United States Patent
Nakayama et al.

(10) Patent No.: US 11,944,492 B2
(45) Date of Patent: Apr. 2, 2024

(54) ULTRASONIC SENSOR ARRAY, GUIDE WIRE, GUIDE WIRE SYSTEM, AND CATHETER

(71) Applicant: ASAHI INTECC CO., LTD., Seto (JP)

(72) Inventors: Tsuyoshi Nakayama, Seto (JP); Kenta Kato, Seto (JP)

(73) Assignee: ASAHI INTECC CO., LTD., Seto (JP)

(*) Notice: Subject to any disclaimer, the term of this patent is extended or adjusted under 35 U.S.C. 154(b) by 104 days.

(21) Appl. No.: 17/547,855

(22) Filed: Dec. 10, 2021

(65) Prior Publication Data
US 2022/0096049 A1    Mar. 31, 2022

Related U.S. Application Data

(63) Continuation of application No. PCT/JP2020/018061, filed on Apr. 28, 2020.

(30) Foreign Application Priority Data

Jun. 21, 2019 (JP) ................. 2019-115293

(51) Int. Cl.
*A61B 8/00* (2006.01)
*A61B 8/12* (2006.01)
*B06B 1/06* (2006.01)

(52) U.S. Cl.
CPC ............... *A61B 8/445* (2013.01); *A61B 8/12* (2013.01); *A61B 8/54* (2013.01); *A61B 8/56* (2013.01); *B06B 1/0607* (2013.01)

(58) Field of Classification Search
CPC .. A61B 8/445; A61B 8/12; A61B 8/54; A61B 8/56; B06B 1/0607
See application file for complete search history.

(56) References Cited

U.S. PATENT DOCUMENTS 4,967,753 A   11/1990 Haase et al.
5,105,818 A    4/1992 Christian et al.
(Continued)

FOREIGN PATENT DOCUMENTS

CN   106664493 A    5/2017
JP   H03-205040 A   9/1991
(Continued)

OTHER PUBLICATIONS

Y. Haga, et al. "Small Diameter Active Catheter Using Shape Memory Alloy", Micro Electro Mechanical Systems, 1998. MEMS 98. Proceedings., Germany Jan. 25-29, 1998, New York, NY, USA, IEEE, US, pp. 419-424, Jan. 25, 1998.
(Continued)

*Primary Examiner* — Serkan Akar
*Assistant Examiner* — Amal Aly Farag
(74) *Attorney, Agent, or Firm* — Oliff PLC

(57) ABSTRACT

A medical ultrasonic sensor array includes a plurality of ultrasonic sensors having a plurality of first electrode plates, a plurality of piezoelectric elements, and a second electrode plate. Each of the ultrasonic sensors has a first electrode plate and a piezoelectric element sandwiched between the second electrode plate and the first electrode plate. Each first electrode plate of each ultrasonic sensor is separated from each other first electrode plate of each other ultrasonic sensor. The second electrode plate is a single body electrode plate shared by the plurality of the ultrasonic sensors. The second electrode plate includes a plurality of cavities, each cavity being formed in a surface of the second electrode plate at which the piezoelectric elements connect to the second electrode plate at a position between connection regions connecting a respective pair of the piezoelectric elements to the second electrode plate.

3 Claims, 24 Drawing Sheets

(56) References Cited

U.S. PATENT DOCUMENTS

| | | | |
|---|---|---|---|
| 5,161,537 A | 11/1992 | Hashimoto et al. | |
| 5,163,445 A | 11/1992 | Christian et al. | |
| 5,174,295 A | 12/1992 | Christian et al. | |
| 5,857,974 A | 1/1999 | Eberle et al. | |
| 6,283,951 B1* | 9/2001 | Flaherty | A61B 17/12172 604/164.11 |
| 2006/0103265 A1 | 5/2006 | Miyoshi | |
| 2006/0235299 A1* | 10/2006 | Martinelli | A61B 8/445 600/434 |
| 2010/0168568 A1* | 7/2010 | Sliwa | A61N 7/022 604/20 |
| 2010/0168583 A1* | 7/2010 | Dausch | B06B 1/0622 600/466 |
| 2014/0236017 A1 | 8/2014 | Degertekin et al. | |
| 2015/0272615 A1* | 10/2015 | Newhauser | A61B 17/320783 606/159 |
| 2015/0297097 A1 | 10/2015 | Matsubara et al. | |
| 2017/0156691 A1 | 6/2017 | Cabrera-Munoz et al. | |
| 2017/0157647 A1 | 6/2017 | Kojima | |
| 2017/0238903 A1* | 8/2017 | Wood | A61B 17/3478 |
| 2019/0053781 A1* | 2/2019 | Stigall | A61B 8/54 |

FOREIGN PATENT DOCUMENTS

| | | |
|---|---|---|
| JP | H03-275047 A | 12/1991 |
| JP | 108-112289 A | 5/1996 |
| JP | H10-192281 A | 7/1998 |
| JP | H11-056857 A | 3/1999 |
| JP | 2001-309497 A | 11/2001 |
| JP | 2006-158939 A | 6/2006 |
| JP | 2016-516459 A | 6/2016 |
| JP | 2018-516623 A | 6/2018 |
| WO | 2014/138099 A1 | 9/2014 |
| WO | 2016/165943 A1 | 10/2016 |

OTHER PUBLICATIONS

J. Janjic, et al. "A 2-D Ultrasound Transducer With Front-End ASIC and Low Cable Count For 3-D Forward-Looking Intravascular Imaging: Performance and Characterization", IEEE Transactions on Ultrasonics, Ferroelectrics, and Frequency Control, IEEE, USA, vol. 65, No. 10, pp. 1832-1844, Oct. 1, 2018.

Y. Haga, M. Esashi. "Recent Developments in Ultrasonic Diagnostic Techniques: Micromachine Technique for Ultrasonic Intracelom Scanning". Advanced Medicine, Advanced Medical Technology Research Center, Japan, vol. 5, No. 1. pp. 48-51 (Feb. 1998).

Dec. 21, 2021 English translation of Preliminary Report on Patentability issued in International Patent Application No. PCT/JP2020/018061.

* cited by examiner

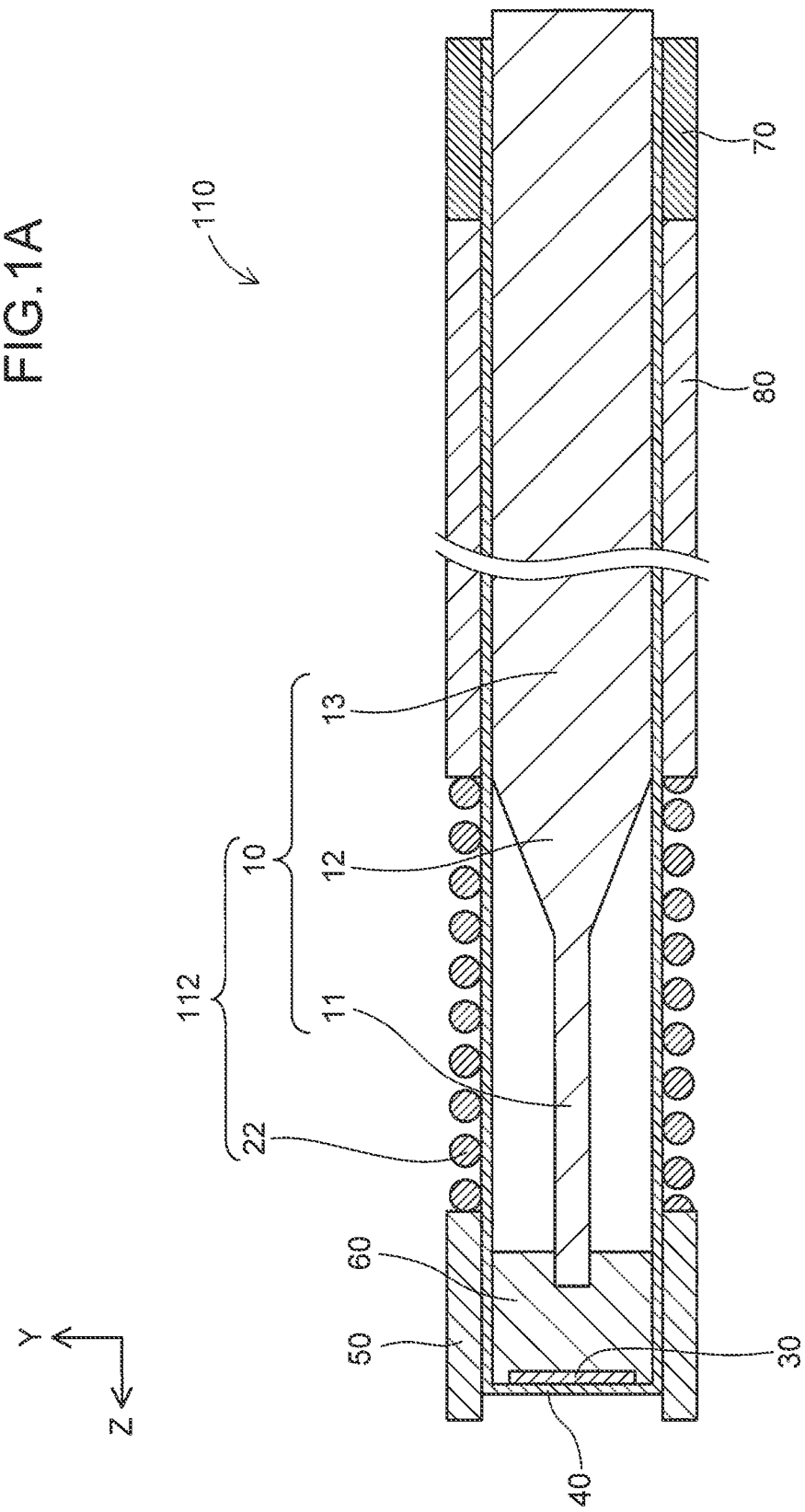

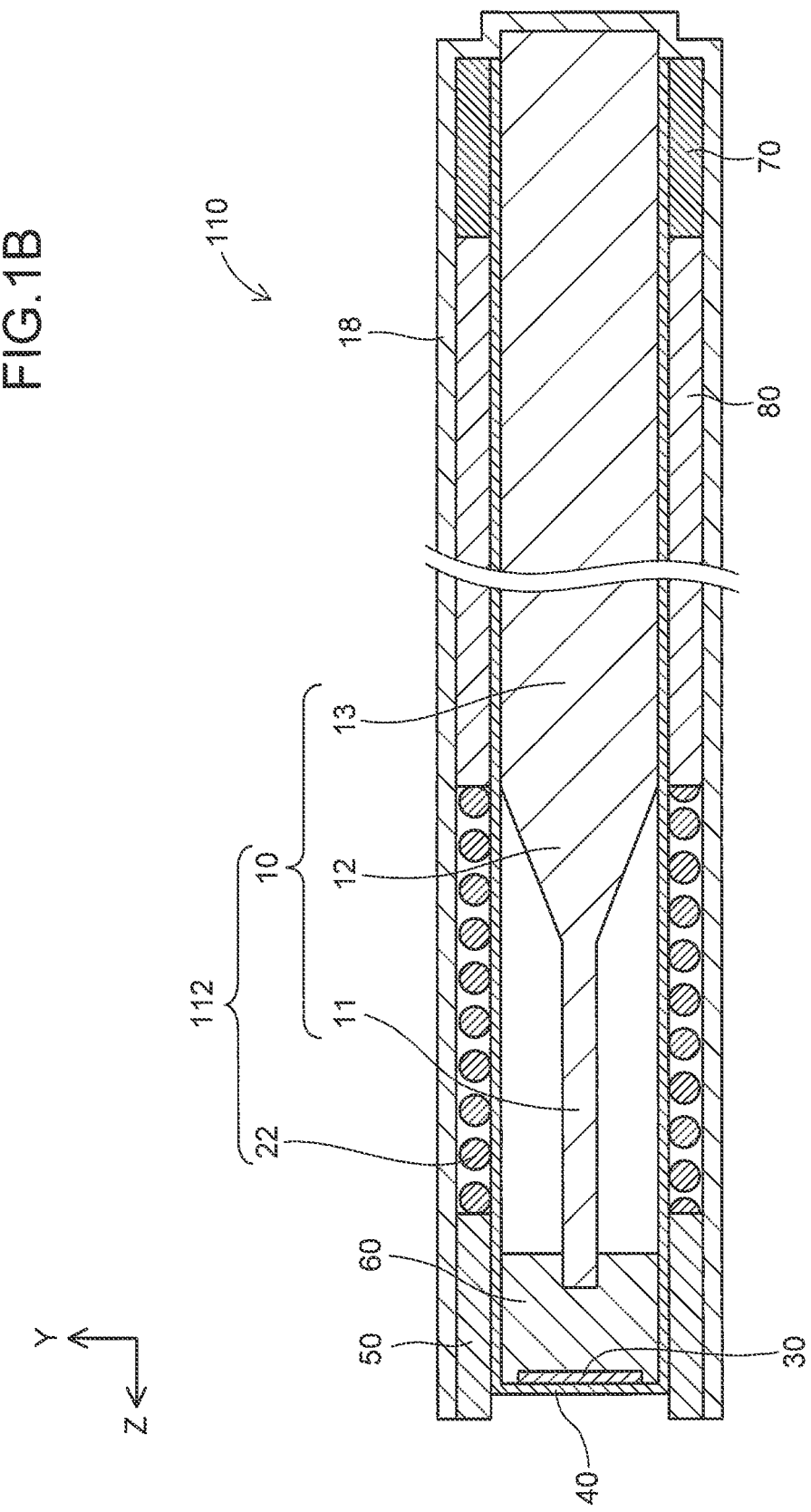

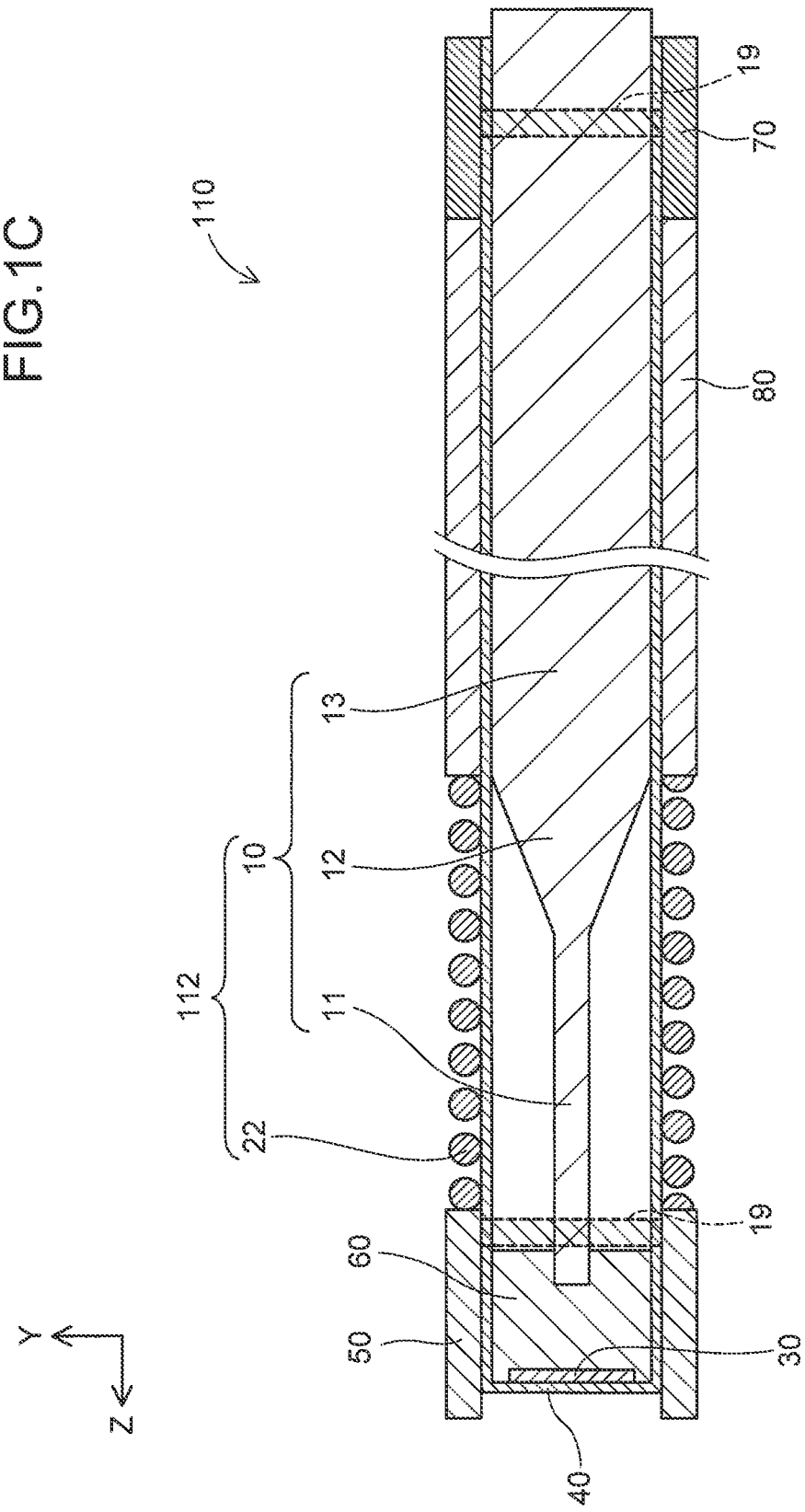

ULTRASONIC SENSOR ARRAY, GUIDE WIRE, GUIDE WIRE SYSTEM, AND CATHETER

CROSS REFERENCE TO RELATED APPLICATIONS

The present application is a Bypass Continuation of PCT/JP2020/018061, filed Apr. 28, 2020, which is based upon and claims priority from JP 2019-115293 filed on Jun. 21, 2019, the entirety of the prior applications being hereby incorporated by reference into this application.

TECHNICAL FIELD

The technology disclosed herein relates to an ultrasonic sensor array, an imaging guide wire, a guide wire system, an imaging catheter, and a catheter system.

BACKGROUND ART

In a procedure for performing a therapy for a heart disease, a physician performing the procedure inserts a guide wire gradually into a constricted part or occluded part (hereinafter referred to as "lesion site") with reference to an image of a blood vessel while imaging the coronary artery with an X-ray fluoroscopic apparatus. A guide wire serves as a kind of track for subsequently bringing a balloon catheter or a stent to a lesion site, and whether the guide wire passes the lesion site contributes greatly to a success rate of the procedure.

In the case of a lesion of chronic total occlusion (hereinafter referred to as "CTO"), which has particular difficulty in passing of a guide wire, a contrast medium fails to pass through an occluded part, which is a lesion, thus preventing obtaining images of the inside of the occluded part as well as a blood vessel beyond the part. In such case, depending on the sensation of the hands, a physician gradually inserts a guide wire with avoiding, e.g., a hard calcified part and exploring a passing route that facilitates passing of the guide wire within a true lumen of a blood vessel. Insertion of a guide wire into an occluded part is thus affected inevitably by experience of a physician. Alternatively, corresponding to conditions of an occluded part and the surrounding blood vessel, a physician also sometimes selects a route that passes through the inside of the vascular wall, rather than passes a guide wire through the inside of an occluded part.

As an example of guide wires that assist diagnosis of a lesion site with lack of information of a blood vessel, such as CTO, a guide wire is known which is to be inserted into a lesion site with being attached to an ultrasonic sensor on the distal end and monitoring information of hardness of the lesion site or blood flow from the echo information thus obtained (see, e.g., Patent Literatures 1, 2, and 3).

A method of checking an anterior image within a blood vessel is effective as a way of identifying spatial information of the blood vessel for the traveling direction of a guide wire. Patent Literature 1 and Patent Literature 2 describe a method of imaging by attaching an ultrasonic sensor element to the distal end of a guide wire and using ultrasonic echo. When one ultrasonic sensor element is used to emit ultrasound and detect ultrasonic echo as described in Patent Literature 1 and Patent Literature 2, the ultrasonic sensor element needs a duration of time until stop of vibration of the ultrasonic sensor element itself during emission and reception. An ultrasonic sensor element therefore needs a duration of time for switching from emission to reception, and makes it difficult to obtain a high-definition anterior image in a close distance.

Meanwhile, Patent Literature 3 describes attachment of a plurality of sensing components including an ultrasonic sensor. Such configuration allows use of separate sensing components for emission and reception, and the sensing component does not need a duration of time for switching from emission to reception. However, the configuration described in Patent Literature 3 has some problems of attachment of the plurality of sensing components due to a guide wire having a small diameter.

CITATION LIST

Patent Literature

Patent Literature 1: Japanese Patent Application Laid-open Publication No. 1996-112289
Patent Literature 2: Japanese Patent Application Laid-open Publication No. 1991-205040
Patent Literature 3: Japanese Patent Application Laid-open Publication (Translation of PCT Application) No. 2018-516623

SUMMARY

The first problem relates to reception signal delay. For the purpose of obtaining a high-definition image with a small cross-sectional area (opening width), it is necessary that an ultrasonic sensor array including a highly dense arrangement of a plurality of ultrasonic sensor elements having high frequency (10 to 50 MHz) be attached to the distal end of a guide wire in order to compensate a disadvantage of the small opening width and thus reduction in bearing resolution. When a plurality of separate ultrasonic sensor elements is used to configure an ultrasonic sensor array, a position gap is generated between respective positions of the ultrasonic sensor elements, resulting in signal reception delay between the respective ultrasonic sensors. Such signal reception delay reduces definition of an image of a blood vessel, and thus is not preferable. Japanese Patent Application Laid-open Publication (Translation of PCT Application) No. 2018-516623 describes attachment of a plurality of sensing components to the distal end of a guide wire, but does not describe any specific means for solution for a position gap in an arrangement of the sensing components and signal reception delay generated from the position gap.

The second problem relates to generation of mechanical cross talk. In an ultrasonic sensor array including a highly dense arrangement of ultrasonic sensor elements on a sender part and a receiver part, mechanical vibration is conveyed between an ultrasonic sensor element on the sender part and an ultrasonic sensor element on the receiver part, thereby generating mechanical cross talk. Such generation of mechanical cross talk reduces definition of an image of a blood vessel, and thus is not preferable. Japanese Patent Application Laid-open Publication (Translation of PCT Application) No. 2018-516623 describes attachment of a plurality of sensing components to the distal end of a guide wire, but does not describe any specific means for solution for this mechanical cross talk.

The third problem relates to electrical cross talk generated by conveyance of a signal. Japanese Patent Application Laid-open Publication (Translation of PCT Application) No. 2018-516623 describes that a plurality of electric conductors connected to a plurality of sensing components is wound around a shaft of a guide wire. However, when a signal is applied to the electric conductors described in Japanese Patent Application Laid-open Publication (Translation of PCT Application) No. 2018-516623, which are arranged in a relatively close interval, electrical cross talk occurs where variation of current running through the electric conductor having application of the signal causes a change of current in another electric conductor. Such occurrence of electrical cross talk appears as deterioration of a signal running in another electric conductor, results in reduction in definition of an image of a blood vessel, and thus is not preferable.

In general, a coaxial line, a shielded wire, or the like is used for prevention of electrical cross talk. At the same time, a shaft at the distal end of a guide wire is required to have flexibility and a small diameter. For example, when a thick signal line such as a coaxial line is used with winding around a shaft of a guide wire, the guide wire has a larger transverse cross section diameter, causing reduction in passage property in a blood vessel. Moreover, in arrangement with a shaft of a guide wire, the presence of the coaxial line makes a difference in rigidity corresponding to a direction within a transverse cross section of the guide wire, causing reduction in flexibility for the guide wire to bend along a curvature of a blood vessel. In a guide wire, therefore, it is difficult to use a thick signal line, such as a coaxial line, for conveying a signal obtained with an ultrasonic sensor array disposed at the distal end. However, Japanese Patent Application Laid-open Publication (Translation of PCT Application) No. 2018-516623 does not describe any specific means for solution for electrical cross talk.

The fourth problem relates to reflection of an electric signal generated at the end terminal part of a signal line. An electric signal conveyed through a signal line generates reflection at the end terminal part of a signal line or at a site where change of impedance of the signal line occurs (e.g., a site where a connection of the signal line is changed), and the reflected signal triggers a phenomenon that distorts voltage variation of the electric signal itself within the signal line. Such distortion of voltage variance due to reflection appears as deterioration of a signal running in the signal line, results in reduction in definition of an image of a blood vessel, and thus is not preferable. Japanese Patent Application Laid-open Publication (Translation of PCT Application) No. 2018-516623 does not describe any specific means for solution for this reflection of an electric signal.

Herein, a technology will be disclosed which provides a solution to each of the problems described above.

Solution to Problem

The technology disclosed herein can be realized by, e.g., the following aspects.

(1) The ultrasonic sensor array disclosed herein is a medical ultrasonic sensor array including a plurality of ultrasonic sensors, wherein each of the ultrasonic sensors has a piezoelectric element, and a first electrode plate and a second electrode plate placed so as to sandwich the piezoelectric element, wherein the first electrode plate is separated corresponding to each of the plurality of ultrasonic sensors, wherein the second electrode plate represents a single body of the second electrode plate shared by the plurality of ultrasonic sensors, wherein the second electrode plate is not cut, or is cut in a part in a direction of thickness from the surface of a side having placement of each of the piezoelectric elements, at a position between a connection region to a first piezoelectric element and a connection region to a second piezoelectric element. The ultrasonic sensor array provides inclusion of a structure in which the plurality of ultrasonic sensors leaves a shared portion uncut in a direction of thickness of a second electrode plate by preparing one ultrasonic sensor matrix material, cutting the piezoelectric element from a side of the first electrode plate, and not cutting the second electrode plate or partly cutting it through in a direction of the thickness of the second electrode plate. This allows prevention of a position gap in an arrangement plane on which the plurality of ultrasonic sensors configuring the ultrasonic sensor array is arranged. Consequently, it is possible to prevent a lag of timing of sending and reception of an ultrasonic signal due to a position gap among the plurality of ultrasonic sensors.

(2) In the ultrasonic sensor array described above and between a first ultrasonic sensor and a second ultrasonic sensor adjacent to each other, the second electrode plate is cut over at least a part in a direction of thickness from the surface of a side having placement of each of the piezoelectric elements, at a position between a connection region to the piezoelectric element of the first ultrasonic sensor and a connection region to the piezoelectric element of the second ultrasonic sensor. The ultrasonic sensor array has a cut on the surface of the side having placement of each of the piezo-electric elements in the second electrode plate, thus enabling prevention of vibration of a piezoelectric element of a certain ultrasonic sensor from transmitting in an alignment direction of ultrasonic sensors via the second electrode plate. Consequently, it is possible to prevent generation of mechanical cross talk in which a piezoelectric element of another adjacent ultrasonic sensor also vibrates.

(3) The ultrasonic sensor array described above may further be configured to have a non-oscillatory part that is placed at a position surrounded by the plurality of ultrasonic sensors and shares the second electrode plate; wherein the second electrode plate is not cut, or is cut over a part in a direction of thickness, at a position between the first ultrasonic sensor and the non-oscillatory part; and wherein a cut is made over the whole in a direction of thickness from the surface of a side having placement of each of the piezoelectric elements, at a position between a connection region to the piezoelectric element of the first ultrasonic sensor and a connection region to the piezoelectric element of the second ultrasonic sensor. In the ultrasonic sensor array, even when a piezoelectric element of one ultrasonic sensor vibrates, the vibration is not conveyed directly to another ultrasonic sensor but conveyed to a non-oscillatory part, and attenuates at the non-oscillatory part, thus enabling prevention of the vibration from transmitting to a piezoelectric element of another ultrasonic sensor, and consequently allowing effective prevention of generation of mechanical cross talk in which a piezoelectric element of another ultrasonic sensor also vibrates.

(4) The guide wire disclosed herein may be configured to include a guide wire body, and the above-mentioned ultrasonic sensor array placed at the distal end part of the guide wire body, wherein the ultrasonic sensor array is placed such that an ultrasonic sender-receiver face of each of the ultrasonic sensors directs forward in a direction of insertion of the guide wire body. The guide wire has the ultrasonic sensor array placed at the distal end part of the guide wire body in a forward viewing manner in the guide wire having a relatively small diameter, thus allows the ultrasonic sensor array to easily burrow into a thrombus, and enables achievement to obtain high-definition image information of the inside of the thrombus with use of the ultrasonic sensor array.

(5) The guide wire described above may be configured such that the guide wire body includes a metallic core shaft, and that the second electrode plate of the ultrasonic sensor array is electrically connected to the core shaft. The guide wire enables use of the core shaft as a standard potential line electrically connected to the plurality of ultrasonic sensors, and allows achievement to simplify a configuration of an apparatus.

(6) The guide wire described above may further be configured to include an electrode terminal portion placed at the proximal end part of the guide wire body, and a signal transmission portion that transmits a signal between the first electrode plates of each of the plurality of ultrasonic sensors and the electrode terminal portion; wherein the signal transmission portion includes a signal line individually disposed for each of the plurality of ultrasonic sensors, and wherein the signal line transmits a sent electric signal to be input to the ultrasonic sensor for sending ultrasound, from the electrode terminal portion to the ultrasonic sensor, and also transmits a received electric signal output from the ultrasonic sensor corresponding to received ultrasound, from the ultrasonic sensor to the electrode terminal portion. The guide wire enables achievement of signal transmission between the electrode terminal portion and the ultrasonic sensor without using an IC or the like that controls signal transmission for each of the ultrasonic sensors, thus allowing avoidance of limited voltage value associated with use of an IC or the like, and providing avoidance of shallower exploration depth of each of the ultrasonic sensors due to the limited voltage value.

(7) The guide wire described above may be configured such that the signal transmission portion has arrangement of a plurality of signal lines connected to the ultrasonic sensor array, and includes a constant-voltage wiring placed between one of the signal lines (a first signal line) disposed for one of the ultrasonic sensors, and another of the signal lines (a second signal line) disposed for another of the ultrasonic sensors. The constant-voltage wiring may also be connected to a standard potential line. With such configuration, the degree of variation of voltage generated in the second signal line is to be determined by the degree of variation of voltage generated in the constant-voltage wiring caused by current running in the first signal line, thus providing less electrical cross talk. Accordingly, arrangement of the plurality of signal lines also enables prevention of generation of electrical cross talk between the first signal line disposed for one ultrasonic sensor and the second signal line disposed for another ultrasonic sensor, and allows achievement to obtain high-definition image information of a blood vessel with use of the ultrasonic sensor array.

(8) The guide wire system disclosed herein may be configured to include the guide wire described above, and a control apparatus that has a connection terminal portion electrically connected to the electrode terminal portion of the guide wire and controls the signal transmission; wherein the control apparatus includes a display control section that makes a display section display an image showing a condition of a blood vessel on the basis of the received electric signal output from each of the ultrasonic sensors. The guide wire system enables achievement to display a high-definition image showing a condition of a blood vessel (e.g., a condition of a thrombus) with use of the ultrasonic sensor array.

(9) The guide wire system described above may be configured such that the control apparatus further has an end terminal resistance circuit; a first switching circuit that successively selects one of the received electric signals among the received electric signals received respectively from the signal lines connected via the electrode terminal portion and the connection terminal portion, and sends it to the display control section; and a second switching circuit that selects each remaining of the received electric signals unselected by the first switching circuit, among the received electric signals received respectively from the signal lines connected via the electrode terminal portion and the connection terminal portion, and sends it to the end terminal resistance circuit. In the guide wire system, prevention of generation of reflection of a signal at the end terminal part of the signal line enables effective prevention of generation of signal distortion due to reflection at the end terminal part of the signal line, and allows achievement to obtain higher-definition image information with use of the ultrasonic sensor array.

(10) The guide wire system may be configured such that the control apparatus includes a signal correction section that corrects the received electric signal transmitted by one of the signal lines on the basis of a value preset as the amount of electrical cross talk between the one of the signal lines disposed for one of the ultrasonic sensors and another of the signal lines disposed for another of the ultrasonic sensors. The guide wire system identifies the amount of electrical cross talk generated in a signal line due to a configuration of the system and variation of the environment surrounding the system and corrects the received electric signal, thereby enabling mitigation of effect of the electrical cross talk, and allowing achievement to obtain higher-definition image information with use of the ultrasonic sensor array.

(11) The catheter disclosed herein may be configured to include a catheter body, and the above-mentioned ultrasonic sensor array placed at the distal end part of the catheter body; wherein the ultrasonic sensor array is placed such that an ultrasonic sender-receiver face of each of the ultrasonic sensors directs forward in a direction of insertion of the catheter body. The catheter enables prevention of occurrence of reduction in definition of an image due to signal reception delay, mechanical cross talk, and electrical cross talk between the ultrasonic sensors.

(12) The catheter described above may be configured such that the catheter body includes a metallic reinforcing body, and that the second electrode plate of the ultrasonic sensor array is electrically connected to the reinforcing body. The catheter enables use of a reinforcing body as a standard potential line electrically connected to the plurality of ultrasonic sensors, and allows achievement to simplify a configuration of an apparatus.

The technology disclosed herein can be realized in a variety of aspects, such as an ultrasonic sensor array, a guide wire (imaging guide wire) or a catheter (imaging catheter) including an ultrasonic sensor array, a system (guide wire system or catheter system) including a guide wire or a catheter and a control apparatus, and a production method thereof.

BRIEF DESCRIPTION OF DRAWINGS

FIG. 1A is an explanatory diagram schematically illustrating a configuration of a guide wire 110 in a first embodiment.

FIG. 1B is an explanatory diagram schematically illustrating another configuration of the guide wire 110 in the first embodiment.

FIG. 1C is an explanatory diagram schematically illustrating another configuration of the guide wire 110 in the first embodiment.

DETAILED DESCRIPTION OF EMBODIMENTS

A. FIRST EMBODIMENT

A-1. Configuration of Guide Wire 110

Figure 2:
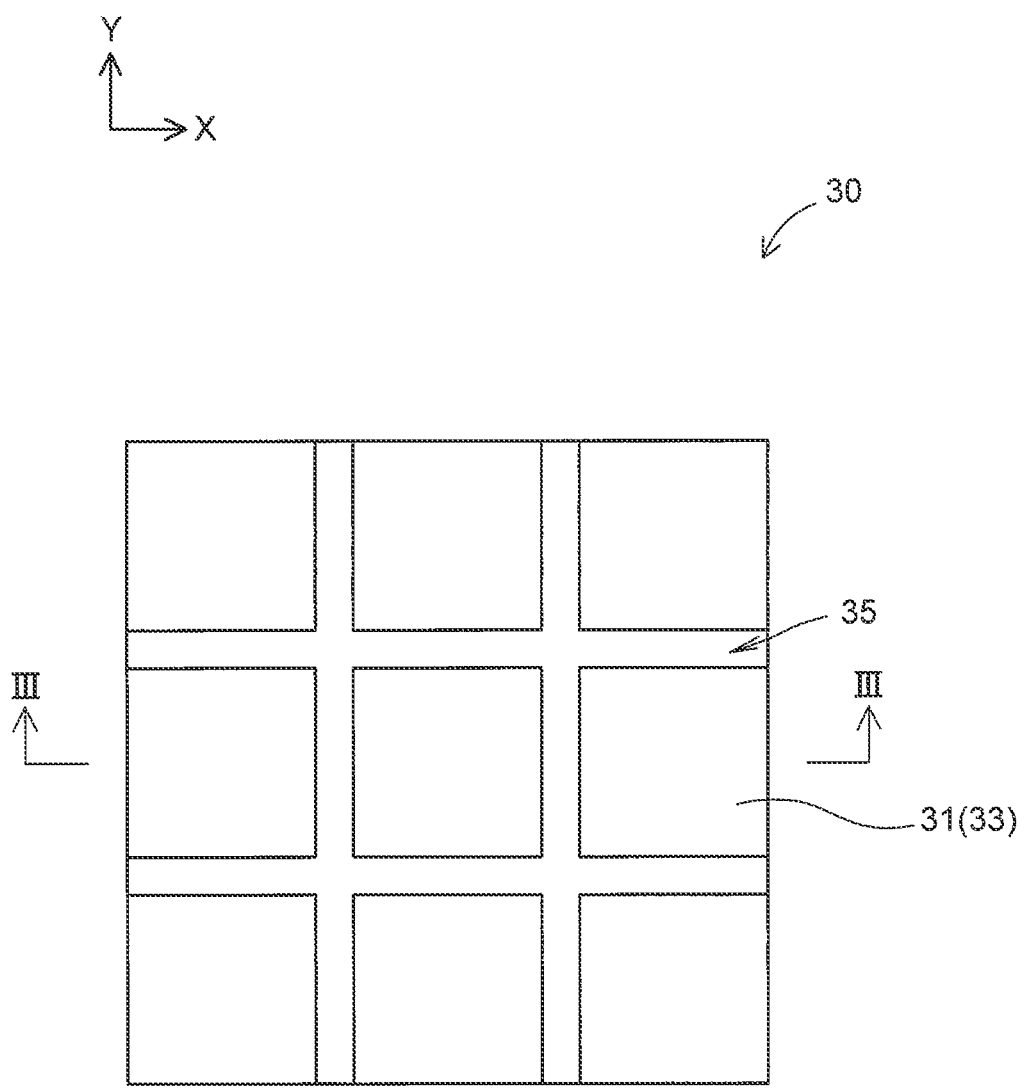
FIG. 2 is an explanatory diagram schematically illustrating a configuration of an ultrasonic sensor array 30 in the embodiment.

FIG. 1A is an explanatory diagram schematically illustrating a configuration of a guide wire 110 in a first embodiment. FIG. 1A depicts a configuration of a vertical cross section (YZ cross section) of the guide wire 110. In FIG. 1A, the forward direction of the Z axis represents a distal end side (far side) to be inserted into the body, and the reverse direction of the Z axis represents a proximal end side (near side) to be manipulated by a technician such as a physician. Although FIG. 1A shows a state where the guide wire 110 takes overall a linear form approximately parallel to the direction of the Z-axis, the guide wire 110 has such flexibility as to be bendable. FIG. 1A also partially omits depiction of the guide wire 110.

The guide wire 110 in the embodiment is an imaging guide wire used for assistance of diagnosis that sends ultrasound into a blood vessel using an ultrasonic sensor, and also receives ultrasound reflected back inside the blood vessel (echo), and visualizes (images) a condition of the blood vessel on the basis of an elapsed time from sending to reception, an amplitude of a reception signal, and the like. The guide wire 110 thus includes a guide wire body 112, and an ultrasonic sensor array 30 placed at the distal end part of the guide wire body 112.

The guide wire body 112 is a wire-shaped apparatus with an overall small diameter (e.g., a diameter of about 0.2 mm-0.5 mm). The guide wire body 112 has a core shaft 10 and a coil body 22. An outer layer of the coil body 22 may have a resin coat layer (polymer jacket) 18 formed of thermoplastic resin selected from the group of urethane-based resins such as polyurethane and amide-based resins such as polyamide, and the resin coat layer may also contain a radiopaque member (see another configuration shown in FIG. 1B). Although the configuration shown in FIG. 1B has the resin coat layer 18 covering the proximal end face of the guide wire 110, the resin coat layer 18 may not cover at least a part of the proximal end face of the guide wire 110.

The core shaft 10 is a rod-shaped member having a small diameter on the distal end side and a large diameter on the proximal end side. More particularly, the core shaft 10 is configured of a rod-shaped small-diameter portion 11 with a circular cross section, a rod-shaped large-diameter portion 13 that is located on the proximal end side relative to the small-diameter portion 11 and has a circular cross section with a larger diameter than the small-diameter portion 11, and a tapered portion 12 that is located between the small-diameter portion 11 and the large-diameter portion 13 and has a diameter inclining to increase from the boundary position with the small-diameter portion 11 toward the boundary position with the large-diameter portion 13. The core shaft 10 is formed of e.g., a metallic material, more particularly stainless steel (such as SUS302, SUS304, or SUS316), superelastic alloy such as Ni—Ti alloy, a piano wire, nickel-chromium-based alloy, cobalt alloy, tungsten, or the like.

The coil body 22 is a coiled member formed as a hollow cylindrical shape by spirally winding a wire. The coil body 22 is placed so as to surround the outer periphery of the distal portion of the core shaft 10 (the small-diameter portion 11 and the tapered portion 12 in the embodiment). The coil body 22 is formed of, e.g., a metallic material, more particularly stainless steel (such as SUS302, SUS304, or SUS316), superelastic alloy such as Ni—Ti alloy, a piano wire, nickel-chromium-based alloy, or radiolucent alloy such as cobalt alloy, radiopacity alloy such as gold, platinum, tungsten, or alloy containing these elements (e.g., platinum-nickel alloy), or the like.

The distal end part of the core shaft 10 of the guide wire body 112 has a backing material (backing load material) 60 disposed thereon. The backing material 60 is a member that supports the ultrasonic sensor array 30 mechanically, and also absorbs unrequisite ultrasound emitted from the ultrasonic sensor array 30, and is formed of, e.g., a resin material.

Figure 3:
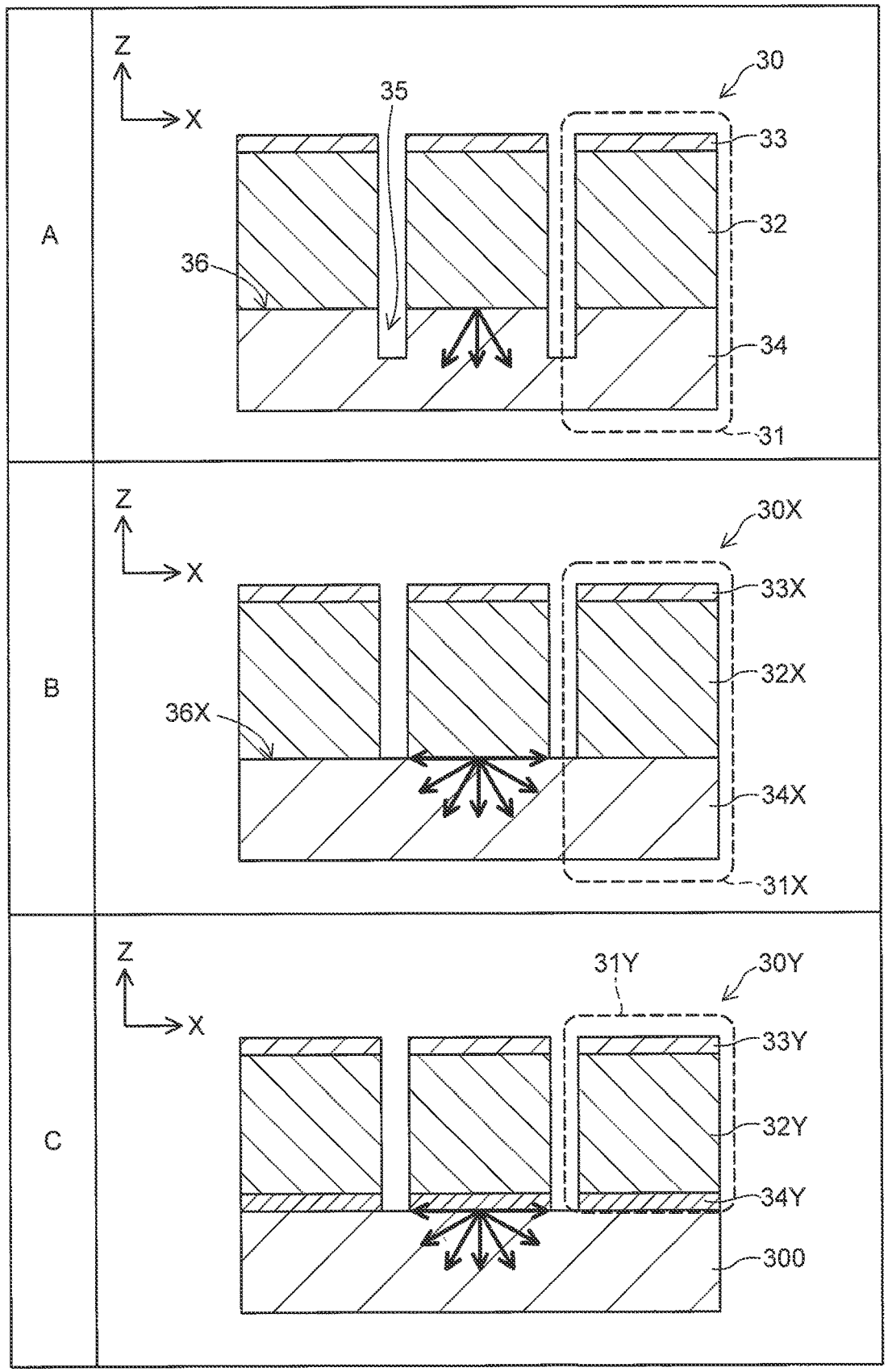
FIG. 3 shows explanatory diagrams schematically illustrating configurations of the ultrasonic sensor array 30 in the embodiment.

FIG. 2 and FIG. 3 are explanatory diagrams schematically illustrating configurations of the ultrasonic sensor array 30 in the embodiment. FIG. 2 depicts a configuration of a plane of the ultrasonic sensor array 30 (XY plane), and panel A of FIG. 3 depicts a configuration of a cross section of the ultrasonic sensor array 30 at a position of III-III in FIG. 2 (XZ cross section). Panel B of FIG. 3 depicts a configuration of a cross section of an ultrasonic sensor array 30X in another configuration described later (XZ cross section). Panel C of FIG. 3 depicts a configuration of a cross section of a conventional ultrasonic sensor array 30Y.

The ultrasonic sensor array 30 is an ultrasonic probe (probe) that sends ultrasound on the basis of a sent electric signal, receives ultrasound reflected back inside a blood vessel (echo), and emits a received electric signal. The ultrasonic sensor array 30 is set to have a relatively small size (e.g., 0.5 mm or less in width and height) for installation at the distal end part of the guide wire body 112.

As shown in FIG. 2 and panel A or panel B of FIG. 3, the ultrasonic sensor array 30 or 30X in the embodiment includes a plurality of ultrasonic sensors 31 or 31X arranged two-dimensionally. More particularly, the ultrasonic sensor array 30 or 30X includes a total of nine of the ultrasonic sensors 31 or 31X arranged in three lines in the X-axis direction and in three lines in the Y-axis direction. An ultrasonic sender-receiver face of each of the ultrasonic sensors 31 or 31X is placed so as to direct forward in a direction of insertion of the guide wire body 112 (the forward direction of the Z-axis in the state in FIG. 1A). In other words, the guide wire 110 in the embodiment allows achievement of imaging of forward viewing.

Each of the ultrasonic sensors 31 or 31X has a piezoelectric element 32 or 32X, which is an ultrasonic oscillator, and a first electrode plate 33 or 33X and a second electrode plate 34 or 34X placed so as to sandwich the piezoelectric element 32 or 32X. The piezoelectric elements 32 and 32X are formed of, e.g., a ceramic such as PZT (lead zirconate titanate), and a polymer substrate such as PVDF (polyvinylidene fluoride) or the like. The first electrode plates 33 and 33X and the second electrode plates 34 and 34X are formed of, e.g., an electrically-conductive material such as copper. On the ultrasonic sender-receiver face side of each of the ultrasonic sensors 31 or 31X configuring the ultrasonic sensor array 30 or 30X, an acoustic adjusting layer may be disposed for adjusting acoustic impedance of the piezoelectric element 32 or 32X and that of a living body.

As an ultrasonic oscillator, a MEMS device such as CMUT (capacitive micro-machined ultrasound transducer) may be used in addition to the piezoelectric element 32.

In the ultrasonic sensor array 30 or 30X in the embodiment, the first electrode plate 33 or 33X is separated for each of a plurality of the ultrasonic sensors 31 or 31X, as shown in panel A or panel B of FIG. 3. In other words, an independent one of the first electrode plate 33 or 33X is disposed for each of the ultrasonic sensors 31 or 31X. By contrast, the second electrode plate 34 or 34X has a single body of the second electrode plate 34 or 34X shared by each of the ultrasonic sensors 31 or 31X. In other words, one second electrode plate 34 or 34X functions as the second electrode plate 34 or 34X of all of the ultrasonic sensors 31 or 31X. The second electrode plate 34 or 34X is electrically connected to the metallic core shaft 10, and the potential of each of the second electrode plates 34 and 34X is set to a predetermined standard potential (described as 0 V or GND in the embodiment and the drawings).

In the ultrasonic sensor array 30 shown in panel A of FIG. 3, the second electrode plate 34 shared by each of the ultrasonic sensors 31 has a cavity 35 formed on a surface 36 of a side having placement of each of the piezoelectric elements 32 (the upper face in panel A of FIG. 3), at a position between a connection region to a certain one of the piezoelectric elements 32 (first piezoelectric element) and a connection region to another of the piezoelectric elements 32 (second piezoelectric element). In other words, at this position, the second electrode plate 34 is cut over a part in a direction of thickness from the surface 36 (the direction of the Z axis). Such configuration (a configuration where the second electrode plate 34 is cut over a part in the direction of thickness) is employed at all of the above-mentioned positions in the ultrasonic sensor array 30 shown in panel A of FIG. 3.

As shown in FIG. 1A, the guide wire 110 includes an electrode terminal portion 70 placed at the proximal end part of the guide wire body 112, and an FPC (flexible printed circuits, flexible printed circuit substrate) 40 that transmits a signal between the first electrode plate 33 of each of the ultrasonic sensors 31 configuring the ultrasonic sensor array 30, and the electrode terminal portion 70. The FPC 40 is an example of a signal transmission portion in the claims.

Figure 4:
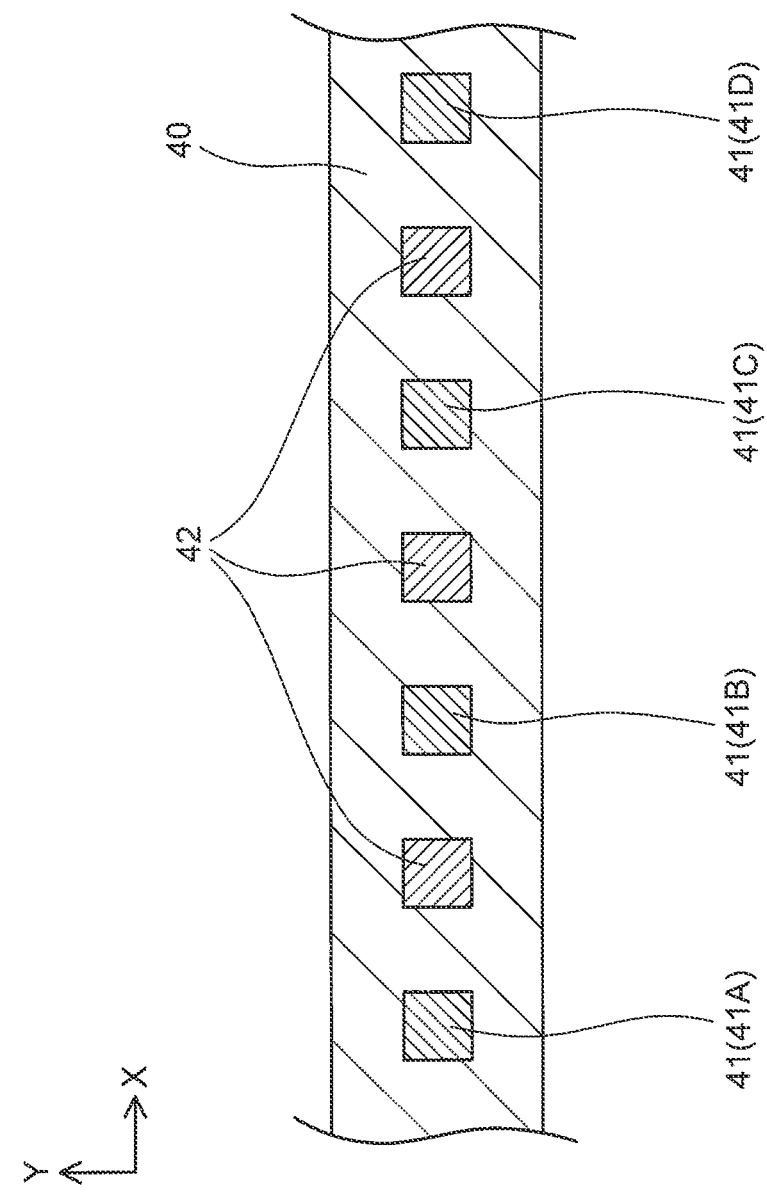
FIG. 4 is an explanatory diagram schematically illustrating a configuration of an FPC 40.

FIG. 4 is an explanatory diagram schematically illustrating a configuration of the FPC 40. FIG. 4 depicts a configuration of a cross section (XY cross section) of a part of the FPC 40. The FPC 40 is a flexible circuit substrate in which a wiring layer formed of an electrically-conductive material such as copper is placed on a base layer formed of an insulative material such as polyimide, and in which a cover layer formed of an insulative material similar to the base layer is placed on the wiring layer. Instead of the FPC 40 in FIG. 4, a ribbon wire may be used which is to take nearly the same structure.

As shown in FIG. 4, the FPC 40 has n signal lines 41 (41A, 41B, 41C, 41D . . . ) in the wiring layer. N is the number of the ultrasonic sensors 31 configuring the ultrasonic sensor array 30, and the embodiment has n=9. Each of the signal lines 41 is individually disposed for each of a plurality of the ultrasonic sensors 31 configuring the ultrasonic sensor array 30 (i.e., a dedicated signal line for each of the ultrasonic sensors 31), and electrically connected to the first electrode plate 33 of each of the ultrasonic sensors 31. Each of the signal lines 41 transmits a sent electric signal to be input to the ultrasonic sensor 31 for sending of ultrasound, from an electrode terminal portion 70 to the ultrasonic sensor 31, and also transmits a received electric signal output from the ultrasonic sensor 31 corresponding to received ultrasound, from the ultrasonic sensor 31 to the electrode terminal portion 70. In the wiring layer, the FPC 40 also has a constant-voltage wiring 42 placed between one of the signal lines 41 (e.g., 41A) disposed for one of the ultrasonic sensors 31 and another of the signal lines 41 (e.g., 41B) disposed for another of the ultrasonic sensors 31. The potential of the constant-voltage wiring 42 is set to a predetermined standard potential (described as 0 V or GND in the embodiment and the drawings).

The constant-voltage wiring 42 is electrically connected to the core shaft 10 at an electrode of the ultrasonic sensor 31 or in the proximity of the tapered portion 12 of the core shaft 10 of the guide wire 110, and also is electrically connected to the core shaft 10 at the electrode terminal portion 70 or within a control apparatus. At that time, as with another configuration as shown in FIG. 1C, two sites of the distal end side and the proximal end side may have electrical connection of the constant-voltage wiring 42 to the core shaft 10 by, e.g., a solder material 19, thereby eliminating the difference in potential between the distal end side and the proximal end side.

In each of the ultrasonic sensors 31, once voltage corresponding to a sent electric signal is applied to the piezoelectric element 32 through the first electrode plate 33 connected to the electrode terminal portion 70 via the signal line 41 of the FPC 40, and the second electrode plate 34 set to a standard potential by electrical connection to the core shaft 10, ultrasound is sent from the piezoelectric element 32 by contraction of the piezoelectric element 32. By contrast, once ultrasound (a reflected wave from the inside of a blood vessel) is received by the piezoelectric element 32, contraction of the piezoelectric element 32 generates voltage between the first electrode plate 33 and the second electrode plate 34, thereby outputting a received electric signal corresponding to received ultrasound toward the electrode terminal portion 70. In the ultrasonic sensor array 30 that has a relatively small size for installation on the guide wire 110 having a relatively small diameter, the frequency of ultrasound sent from the ultrasonic sensor 31 is, for example, preferably 10 MHz or more, and more preferably 20 MHz or more, for improving resolution.

As shown in FIG. 1A, the guide wire 110 includes a housing 50. The housing 50 is an approximately hollow cylindrical member covering the ultrasonic sensor array 30 and a part of the FPC 40 at the distal end part of the guide wire 110, and is formed of e.g., metal. In the embodiment, the housing 50 is joined to the distal end of the coil body 22 by, e.g., welding. The housing 50 protects the ultrasonic sensor array 30 and the FPC 40, and also functions as a distal tip of the guide wire 110. The housing 50 may be a member integrated with the coil body 22 or a resin material.

As shown in FIG. 1A, the guide wire 110 includes an outer shaft 80. The outer shaft 80 is an approximately hollow cylindrical member covering the circumference of the core shaft 10 and the FPC 40 at a part closer to the proximal end side than the coil body 22, and is formed of, e.g., metal. In the embodiment, the outer shaft 80 is joined to the proximal end of the coil body 22 by, e.g., welding. The outer shaft 80 protects the FPC 40, and also functions as a shield for each electric signal. The outer shaft 80 may be a member integrated with the coil body 22.

Figure 5:
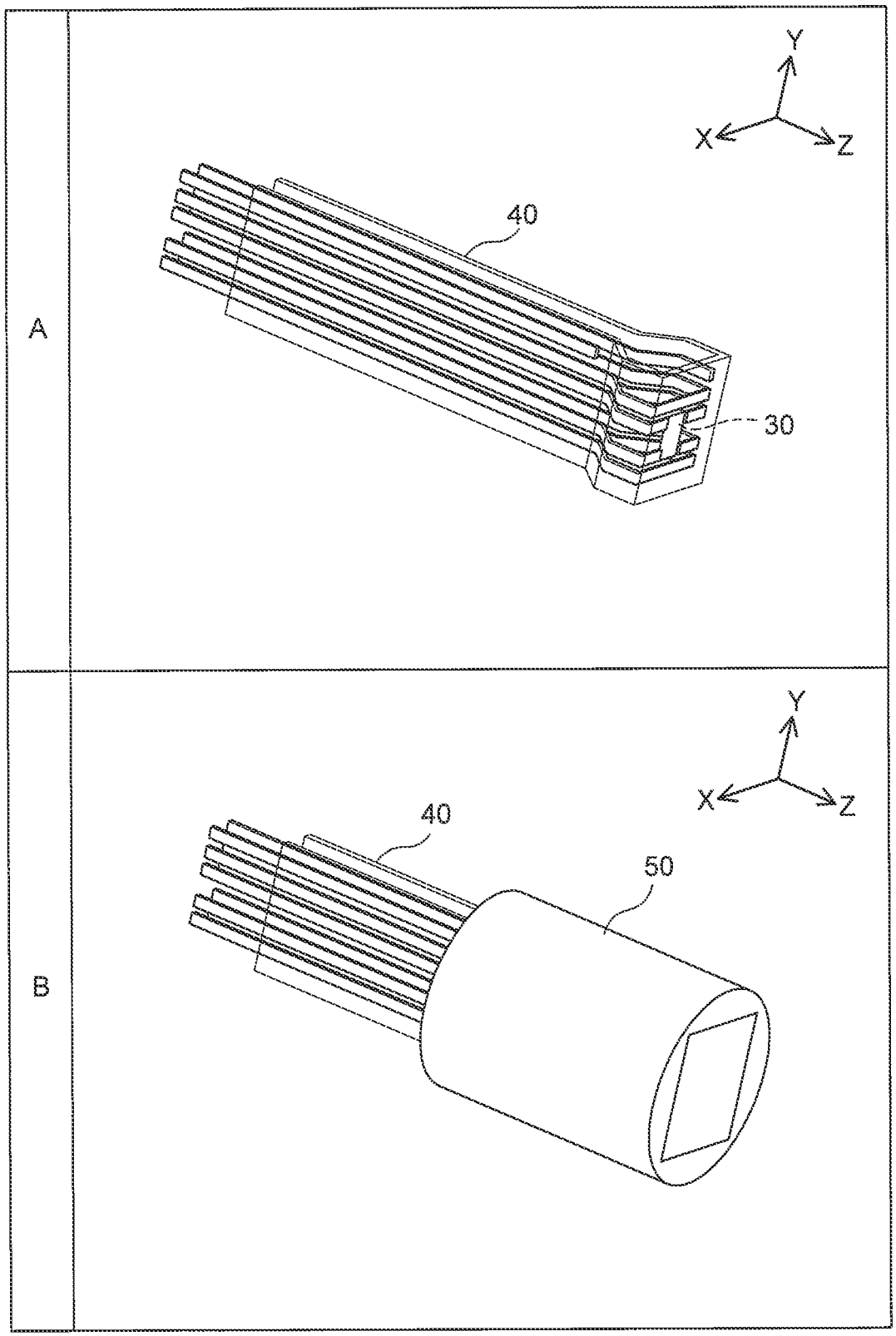
FIG. 5 shows perspective views illustrating configurations of each part in the guide wire 110 in more detail.
Figure 6:
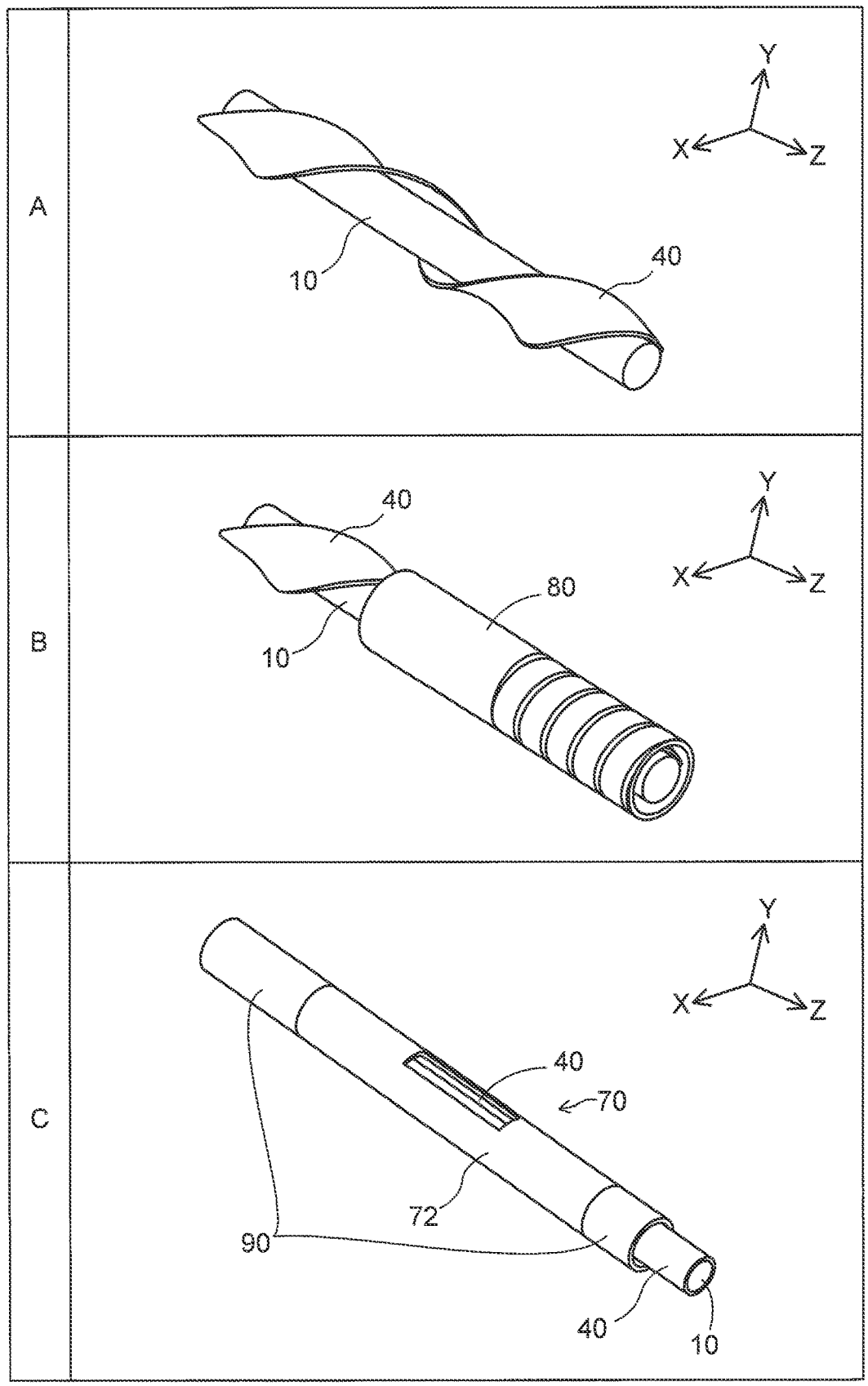
FIG. 6 shows perspective views illustrating configurations of each part in the guide wire 110 in more detail.

FIG. 5 and FIG. 6 are perspective views illustrating configurations of each part in the guide wire 110 described above in more detail. Panel A of FIG. 5 depicts a configuration of the FPC 40 having installation of the ultrasonic sensor array 30, and panel B of FIG. 5 depicts a configuration of the housing 50 covering the FPC 40. As shown in panel A and panel B of FIG. 5, the FPC 40 having installation of the ultrasonic sensor array 30 is bent and contained inside the housing 50.

Panel A and panel B of FIG. 6 depict configurations of the FPC 40 and the outer shaft 80 placed around the core shaft 10. As shown in panel A and panel B of FIG. 6, the FPC 40 is spirally wound around the core shaft 10, and the outer shaft 80 covers the outside of such FPC 40. In the embodiment, since the FPC 40 is spirally wound around the core shaft 10, it is possible to prevent generation of directivity in increment of rigidity of the core shaft 10 due to presence of the FPC 40, enabling prevention of reduction in operability of the guide wire 110.

When the FPC 40 is wound around the core shaft 10, a winding pitch may be an overall uniform pitch or a different pitch between the distal end side and the proximal end side of the core shaft 10, or may be made by winding with a uniform pitch at the distal end side and then changing a pitch from halfway. For example, when the FPC 40 is wound with a uniform pitch overall, the guide wire 110 has no change of rigidity occurring for each place due to the winding of the FPC 40. Nevertheless, varying a winding pitch of the FPC 40 for each place allows the guide wire 110 to achieve rigidity individually required for each place along a long axis. The FPC 40 can be placed with densely winding at a place of presence of the coil body 22, and the FPC 40 can be arranged with the core shaft 10 with sparsely winding or without winding, at a place of absence of the coil body 22 on the proximal end side. At the place of presence of the coil body 22, the guide wire 110 is required to be bendable in any direction along a curvature of a blood vessel, and has a dense winding so as not to generate directivity in increment of rigidity caused by a direction within a transverse cross section. Since a portion with absence of the coil body 22 of the guide wire 110 does not enter the coronary artery, traveling of the guide wire 110 is less affected even when the portion has directivity in increment of rigidity caused by a direction within a transverse cross section; thus, the FPC 40 may be arranged with sparsely winding to a core shaft or without winding.

Alternatively, inside placement of the coil body 22, the FPC 40 may be wound around the core shaft 10, and the FPC 40 may extend along the core shaft 10 at a more proximal end side than the end part of the proximal end side of the coil body 22. In the region where the coil body 22 is placed, such configuration allows obtaining approximately uniform rigidity and flexibility in any direction within a transverse cross section from the center of the core shaft 10, in a transverse cross section of the guide wire 110. On the other hand, a nearer side than the coil body 22 may have such configuration in order to prioritize prevention of deterioration of a signal in the FPC 40 over prevention of variation of rigidity and flexibility in any direction within a transverse cross section due to placement of the FPC 40.

Although panel A of FIG. 6 describes the FPC 40 that winds around the core shaft 10, a ribbon wire can be used to be regularly aligned, thereby obtaining a similar structure. Alternatively, the FPC 40 connected to the ultrasonic sensor array 30 may be wound around the core shaft 10, and then the FPC 40 may be connected to a ribbon wire and changed inside placement of the coil body 22. The change from the FPC 40 to a ribbon wire had better be performed at a site having less change of rigidity along a long axis of the guide wire 110.

Panel C of FIG. 6 depicts a configuration of the electrode terminal portion 70 disposed at the proximal end of the guide wire 110. An area associated with electrode terminal portion 70 has removal of a cover layer (cover lay film) of the FPC 40 wound around the outer periphery of the core shaft 10, and exposure of a wiring layer. The outside of the exposure part of the wiring layer of the FPC 40 has an electrode ring 72 where an opening is formed, and an electrically-conductive paste filled in the opening electrically connects the electrode ring 72 to the wiring layer of the FPC 40. An insulative resin 90 is placed on the distal end side and the proximal end side of the electrode ring 72.

A production method of the ultrasonic sensor array 30 in the embodiment is e.g., as follows. First, a matrix material of an ultrasonic sensor is made by forming a first electrode layer (the first electrode plate 33) as a film on a first surface of a tabular piezoelectric wafer formed of a material of the piezoelectric element 32 (e.g., PZT), as well as forming a second electrode layer (the second electrode plate 34) as a film on a second surface opposed to the first surface of the piezoelectric wafer. Next, a laser is used to cut the first electrode layer and the piezoelectric wafer of the ultrasonic sensor matrix material, thereby dividing the first electrode layer into a plurality of the first electrode plates 33 corresponding to a plurality of the ultrasonic sensors 31, as well as dividing the piezoelectric wafer into a plurality of the piezoelectric elements 32 corresponding to a plurality of the ultrasonic sensors 31. At that time, as described above with reference to panel A of FIG. 3, the surface of the second electrode plate 34 is also cut together so as to form the cavity 35 on the surface 36 of a side having placement of each of the piezoelectric elements 32 in the second electrode plate 34 (a second electrode layer). Alternatively, as described above with reference to panel B of FIG. 3, cutting is finished just upon dividing the piezoelectric wafer into a plurality of piezoelectric elements. In this manner, processing with use of a laser enables creation of the ultrasonic sensor array 30 including a plurality of the ultrasonic sensors 31 despite of having a minute size. The ultrasonic sensor array 30 thus created is placed at a predetermined position on the FPC 40, and joined to the FPC 40 with e.g., an electrically-conductive adhesive.

A-2. Configuration of Guide Wire System 100

Figure 7:
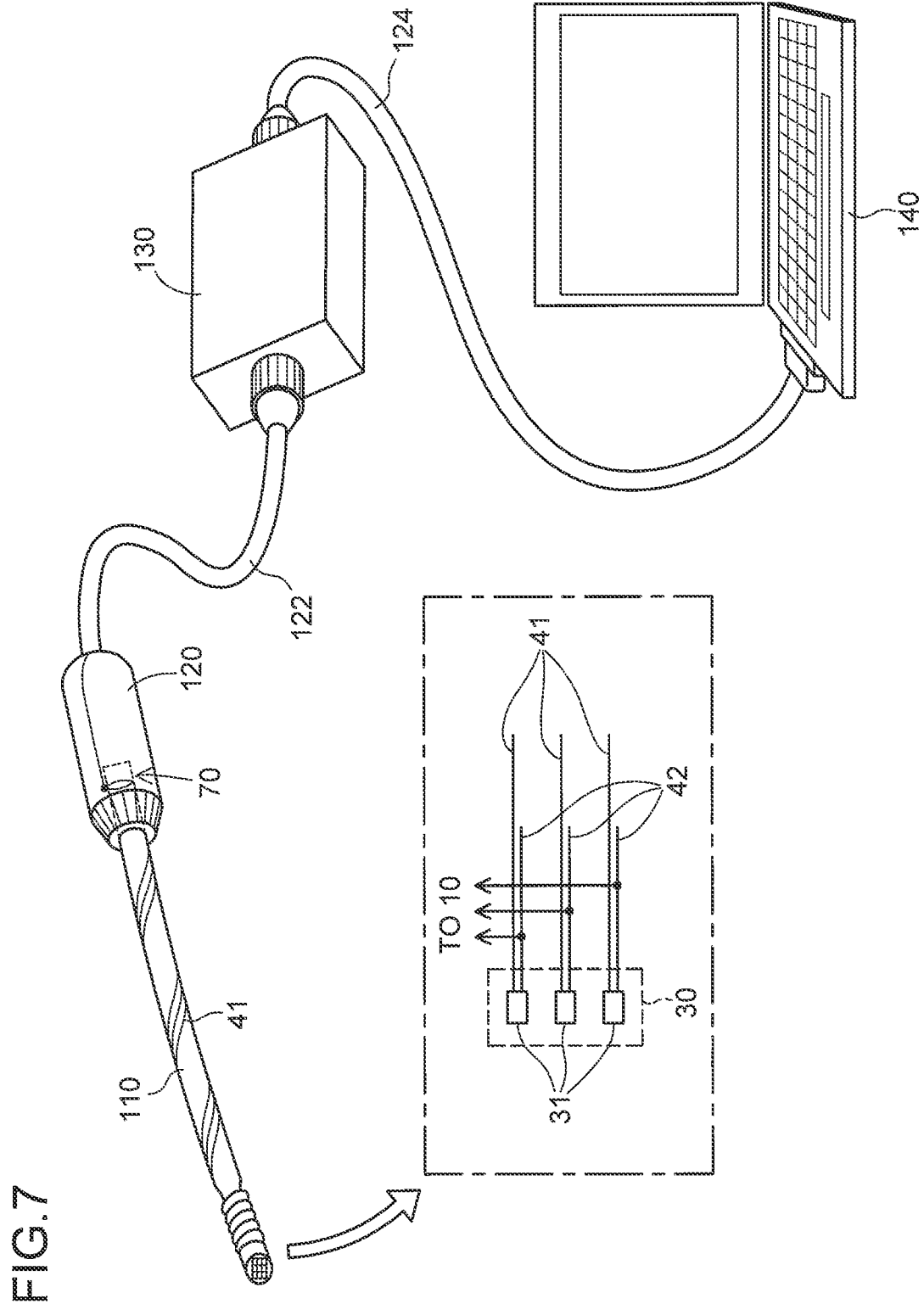
FIG. 7 is an explanatory diagram schematically illustrating a configuration of the guide wire system 100.

Next, description will be made for a configuration of the guide wire system 100 including the guide wire 110 having the configuration described above. FIG. 7 is an explanatory diagram schematically illustrating a configuration of the guide wire system 100. In addition to the guide wire 110, the guide wire system 100 includes a control apparatus 150 that controls transmission of each signal in the guide wire 110.

The control apparatus 150 includes a connector 120, a PIM (patient interface module) 130, and a console 140. Cables 122 and 124 connect the connector 120 to the PIM 130, and the PIM 130 to the console 140. The connector 120 is a connection terminal that is electrically connected to the electrode terminal portion 70 of the guide wire 110 and exchanges each signal with the guide wire 110. The connector 120 is an example of a connection terminal portion in the claims The cable 124 can also be wirelessly connected.

Figure 8:
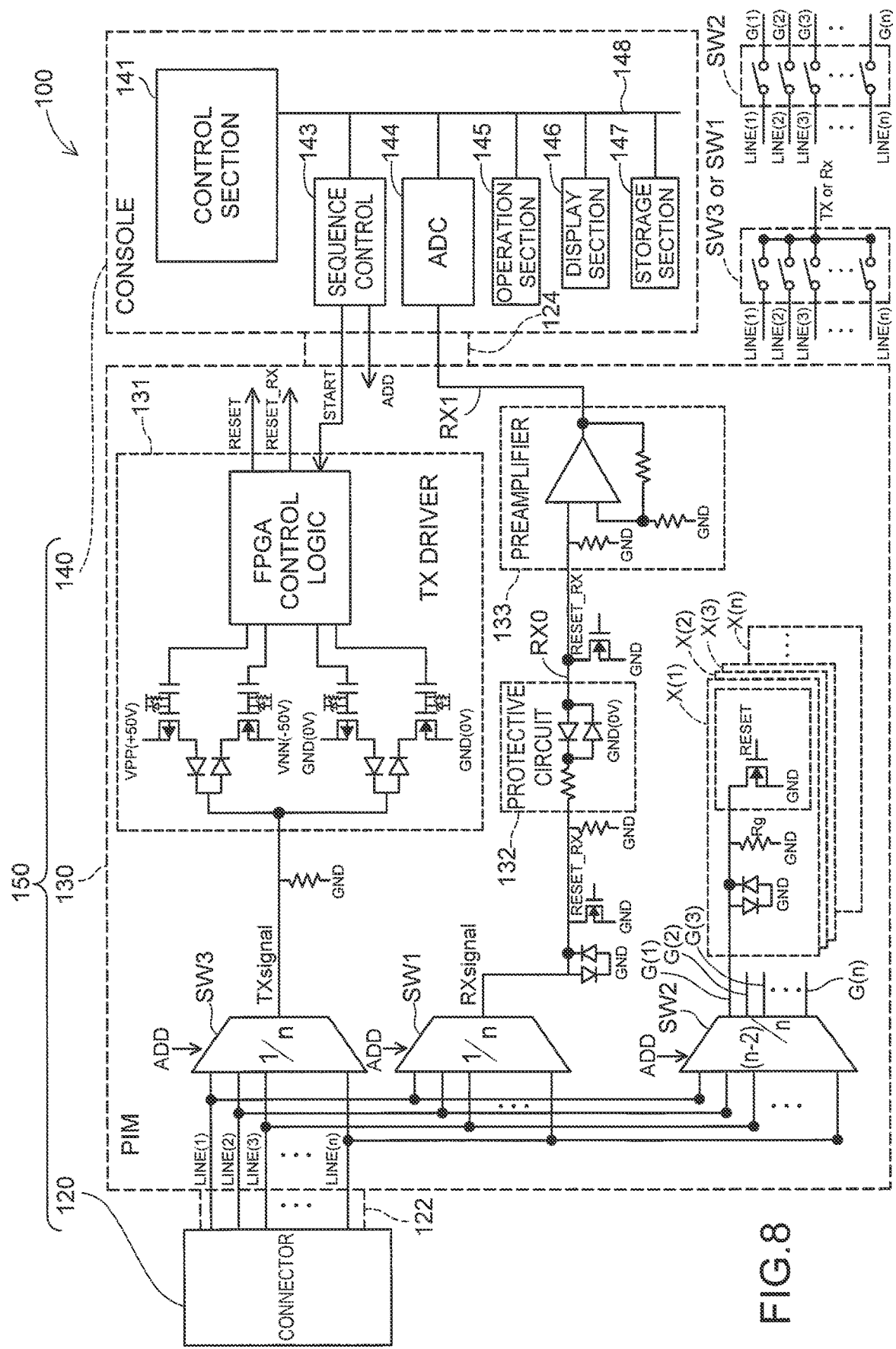
FIG. 8 is an explanatory diagram schematically illustrating an inner configuration of a PIM 130 and a console 140 that configure a control apparatus 150.

FIG. 8 is an explanatory diagram schematically illustrating an inner configuration of the PIM 130 and the console 140 that configure the control apparatus 150. First of all, description will be made for a configuration of the PIM 130. The PIM 130 is an apparatus that mainly controls sending and reception of ultrasound in the guide wire 110. The PIM 130 has n signal lines LINE(1)-LINE(n), which are connected to the connector 120; three switching circuits (first switching circuit SW1, second switching circuit SW2, and third switching circuit SW3), which are connected to the n signal lines LINE(1)-LINE(n); a TX driver 131, which is connected to the third switching circuit SW3 and responsible for sending a sent electric signal; a protective circuit 132 and a preamplifier (preliminary amplifier) 133, which are connected to the first switching circuit SW1 and responsible for receiving a received electric signal; and n end terminal resistance circuits X(1)-X(n), which are connected to the second switching circuit SW2 via n signal lines G(1)-G(n) and have an end terminal resistance Rg for adjusting impedance of a signal line that neither send nor receive ultrasound. As described above, n is the number of the ultrasonic sensors 31 configuring the ultrasonic sensor array 30, and the embodiment has n=9.

Each of the n signal lines LINE(1)-LINE(n) is electrically connected to one of the n signal lines 41 included in the FPC 40 of the guide wire 110, respectively, via the connector 120 and the electrode terminal portion 70 of the guide wire 110. This makes the n lines of signal line LINE(1)-signal line LINE(n) electrically connected to the first electrode plate 33 of one of n ultrasonic sensors 31 configuring the ultrasonic sensor array 30, respectively.

As shown in the lower right panel of FIG. 8, the third switching circuit SW3 successively selects one of the n lines of signal line LINE(1)-signal line LINE(n), and connects the signal line LINE thus selected to the TX driver 131 for sending a sent electric signal. The first switching circuit SW1 successively selects another one of the n lines of signal line LINE(1)-signal line LINE(n), and connects the signal line LINE thus selected to the protective circuit 132 and the preamplifier 133 for receiving a received electric signal. The second switching circuit SW2 selects (n−2) signal lines LINE unselected by both of the third switching circuit SW3 and the first switching circuit SW1 from among the n lines of signal line LINE(1)-signal line LINE(n), and connects the signal lines LINE thus selected to end terminal resistance circuits X, which are responsible for adjusting impedance, via corresponding signal lines G. In the (n−2) signal lines LINE, variation of potential appears due to reflection of a received electric signal from the ultrasonic sensor 31 connected to each signal line or a signal generated in the (n−2) signal lines LINE from the signal line LINE connected to the first switching circuit SW1. Connection of the (n−2) signal lines LINE to the end terminal resistance circuits X enables connection to a predetermined standard potential (described as 0 V or GND in the embodiment and the drawings) without producing additional variation of potential as reflection in the (n−2) signal lines LINE to the variation of potential generated in such signal lines LINE. Although SW3 and SW1 describes an example of switching circuits that select a signal line one by one, a switching circuit that simultaneously selects a plurality of signal lines may be used.

Figure 9:
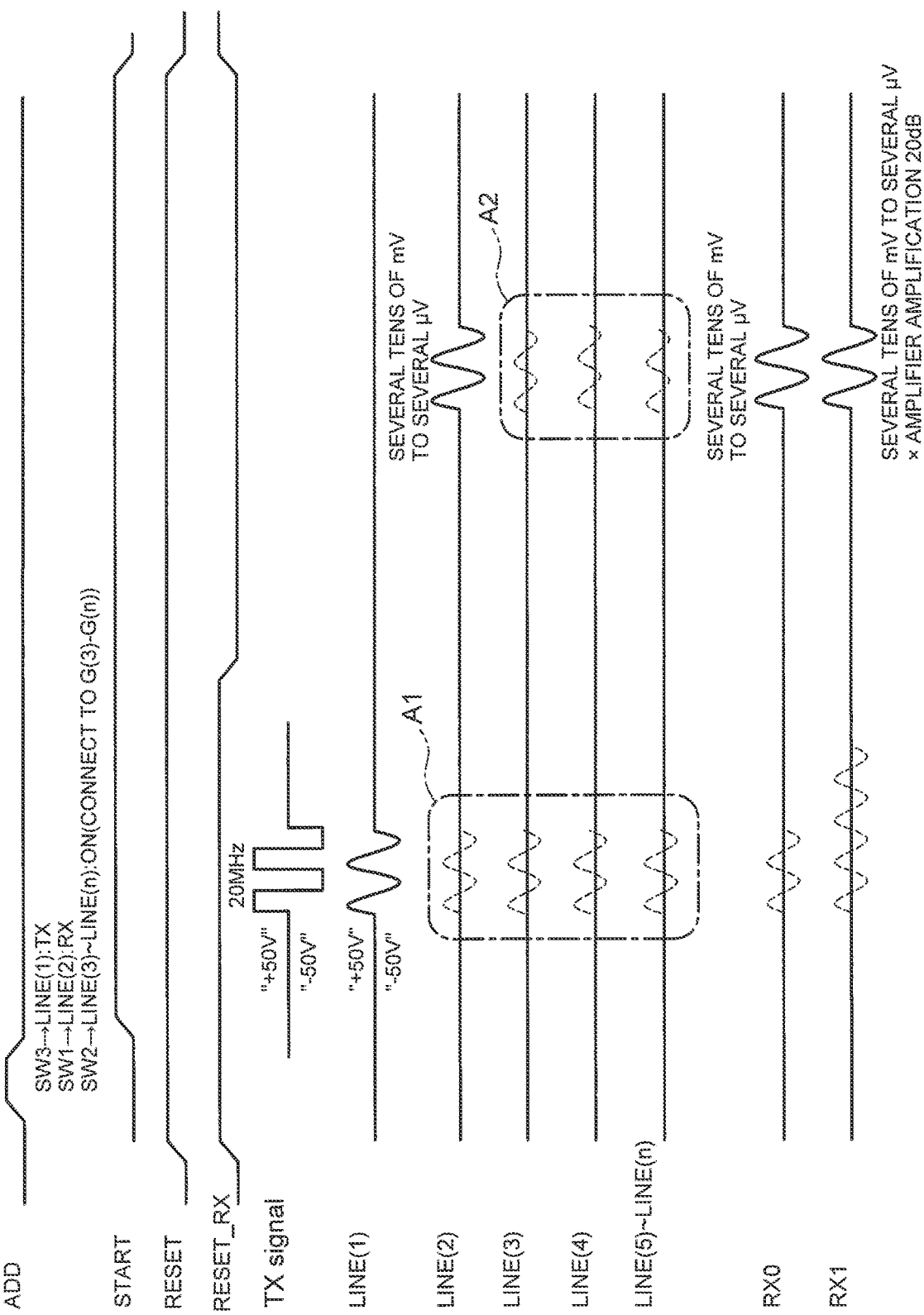
FIG. 9 is a timing chart illustrating an example of actions of the PIM 130.

FIG. 9 is a timing chart illustrating an example of actions of the PIM 130. FIG. 9 shows an example of each signal in a term where the signal line LINE(1) is used for sending ultrasound, where the signal line LINE(2) is used for receiving ultrasound, and where other signal line LINE(3)-signal line LINE(n) are used for neither sending nor receiving ultrasound, among the n lines of signal line LINE(1)-signal line LINE(n), in executing control of the guide wire 110 by the PIM 130.

At timing of switching of ADD signal, which is output from converting console 140, from level L to level H, each of the switching circuits SW1-SW3 selects a signal line LINE. For example, in the example of FIG. 9, the third switching circuit SW3 selects the signal line LINE(1), the first switching circuit SW1 selects the signal line LINE(2), and the second switching circuit SW2 selects the signal lines LINE(3)-LINE(n). This makes the signal line LINE(1) connected to the TX driver 131, the signal line LINE(2) connected to the protective circuit 132 and the preamplifier 133, the signal lines LINE(3)-LINE(n) connected to corresponding of the end terminal resistance circuits X(3)-X(n), respectively. At this point, RESET signal has level H, and the signal lines LINE(3)-LINE(n) connected to the end terminal resistance circuits X(3)-X(n) are in a state of connecting to GND. At this point, RESET RX signal also has level H, and the signal line LINE(2) and the protective circuit 132 are also in a state of connecting to GND.

At timing of switching of START signal, which is output from the console 140, from level L to level H, a sent electric signal TX signal is output from the TX driver 131 toward the third switching circuit SW3. The sent electric signal TX signal is a pulse wave with a predetermined signal level (e.g., +50 V/−50 V) having a predetermined frequency (e.g., 20 MHz). The sent electric signal TX signal is input to the signal line LINE(1) via the third switching circuit SW3. As a result, among a plurality of the ultrasonic sensors 31 configuring the ultrasonic sensor array 30, one of the ultrasonic sensors 31 connected to the signal line LINE(1) via the signal line 41 of the FPC 40 is driven and sends ultrasound. At that time, the signal lines LINE(2)-LINE(n) are connected to GND as described above, thus preventing generation of electrical cross talk between signal lines due to the sent electric signal TX signal input to the signal line LINE(1). That is, for example, in panel A1 of FIG. 9, it is possible to prevent generation of signals in the signal lines LINE(2)-LINE(n) as indicated by dashed lines. This, for example, allows the protective circuit 132 to prevent occurrence of an event that the electrical cross talk causes a signal level to go off the limit, and also allows the preamplifier 133 to prevent occurrence of an event that the electrical cross talk causes a high-level signal to be input to lead to saturation of output and needs a long time for restoration.

Before the earliest timing of receiving a reflected wave (echo) derived by intravascular reflection of ultrasound sent from the ultrasonic sensor 31, RESET_RX signal is switched from level H to level L to prepare receiving of the reflected wave. For example, in reception of a reflected wave from an object located 1 mm away at shortest, switching of RESET_RX signal for preparation of receiving of the reflected wave is made before passing of about 1.3 μs, which is derived by dividing a distance of 1 mm×2 (round trip) by sonic velocity in the living body (about 1500 m/s). A signal of the reflected wave received by the ultrasonic sensor 31 is input as a received electric signal RX signal to the protective circuit 132 via the signal line 41 of the FPC 40, the signal line LINE(2), and the first switching circuit SW1. The received electric signal RX signal is converted to a received electric signal RX0 limited to a predetermined signal level in the protective circuit 132, input to the preamplifier 133, converted to a received electric signal RX1 amplified in the preamplifier 133, and output toward the console 140. At that time, the signal lines LINE(3)-LINE(n) are connected to GND as described above, thus preventing generation of electrical cross talk between signal lines due to transmission of reception signals by the signal line LINE(3)-LINE(n). That is, for example, in panel A2 of FIG. 9, it is possible to prevent generation of signals in the signal lines LINE(3)-LINE(n) as indicated by dashed lines. This, for example, improves accuracy of the received electric signal RX1 output toward the console 140.

After the latest timing of receiving a reflected wave (echo) derived by intravascular reflection of ultrasound sent from the ultrasonic sensor 31, RESET_RX signal is switched from level L to level H to prepare sending of ultrasound for the next sequence. For example, in reception of a reflected wave from an object located 10 mm away at longest, switching of RESET_RX signal for preparation of sending of ultrasound for the next sequence is made after passing of about 13 μs, which is derived by dividing a distance of 10 mm×2 (round trip) by sonic velocity in the living body (about 1500 m/s). Subsequently, processing similar to the processing described above is repeated with switching of selection of a signal line LINE in each of the switching circuits SW1-SW3, and sending and reception of ultrasound is executed by each of the ultrasonic sensors 31 configuring the ultrasonic sensor array 30.

Next, description will be made for a configuration of the console 140. The console 140 is a computer for mainly controlling sequential actions in the PIM 130 described above, as well as performing processing that visualizes (images) a condition of a blood vessel on the basis of the received electric signal RX1 input from the PIM 130. As shown in FIG. 8, the console 140 includes a control section 141, a sequence control circuit 143, an A/D converter (ADC) 144, an operation section 145, a display section 146, and a storage section 147. Each of these sections is connected to each other via a bus 148.

The display section 146 in the console 140 is configured of, e.g., a liquid crystal display, and the like, and displays various kinds of images and information. The operation section 145 is configured of, e.g., a keyboard or a mouse, a button, a microphone, and the like, and receives operation and direction of a manager. The display section 146 may function as the operation section 145 by including a touch panel. The storage section 147 is configured of, e.g., ROM or RAM, a hard disk drive (HDD), and the like, and stores a variety of programs and data, or is used as a working area in execution of various kinds of programs and a temporary storage area of data.

The sequence control circuit 143 in the console 140 outputs the ADD signal and START signal described above toward the PIM 130. The A/D converter 144 converts the received electric signal RX1, which is an analog signal output from the console 140, to a digital signal.

Figure 10:
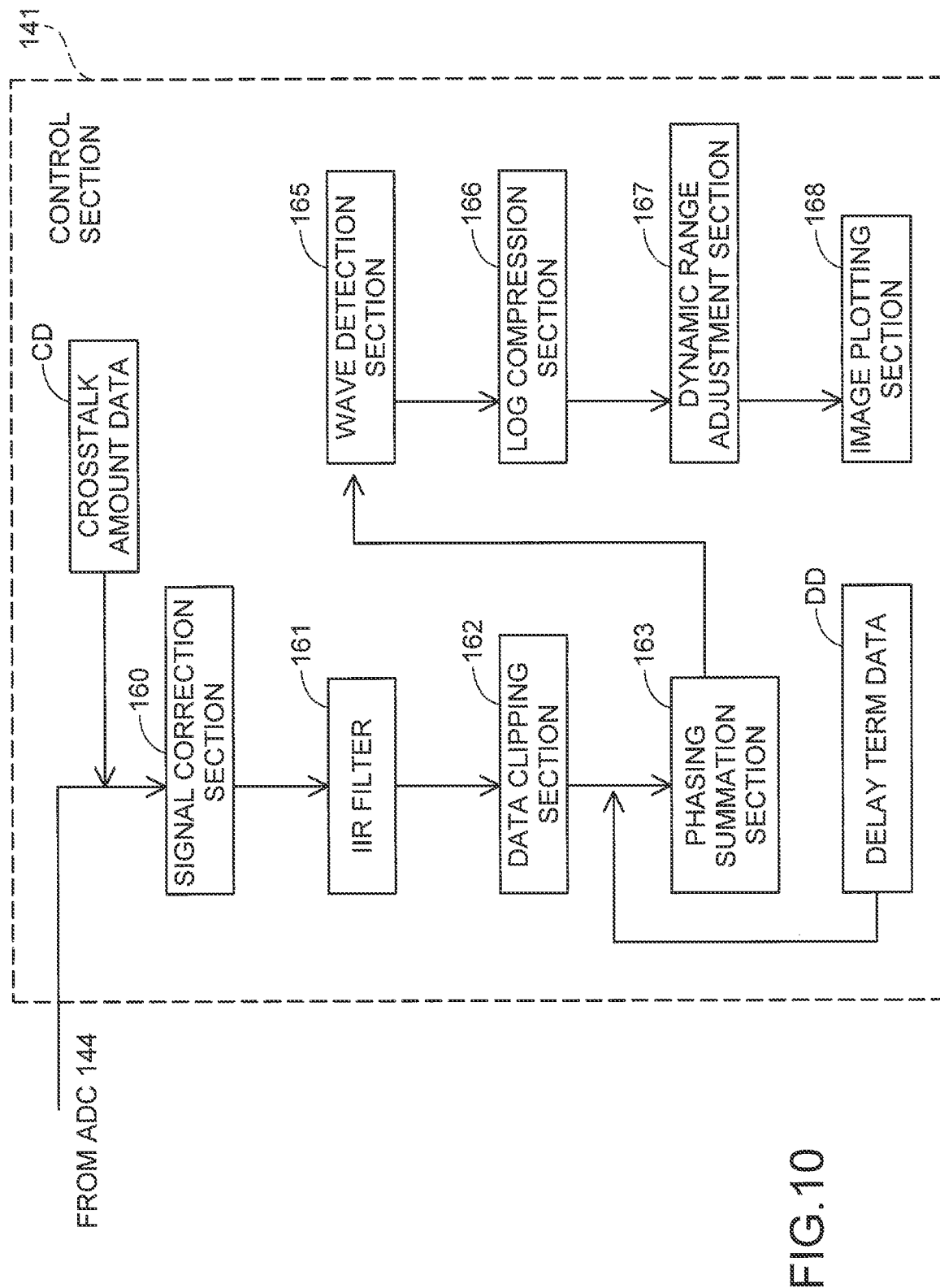
FIG. 10 is an explanatory diagram illustrating a configuration of a control section 141 of the console 140.

The control section 141 in the console 140 is configured of, e.g., CPU, and the like, and controls an action of the console 140 by executing a computer program retrieved from the storage section 147. For example, as shown in FIG. 10, the control section 141 functions as a signal correction section 160, a IIR filter 161, a data clipping section 162, a phasing summation section 163, a wave detection section 165, a log compression section 166, a dynamic range adjustment section 167, and an image plotting section 168. The control section 141 is an example of a display control section in the claims.

Imaging processing by the control section 141 in the console 140 is exemplarily as follows. For the received electric signal RX1 as a digital signal output from the A/D converter 144, the signal correction section 160 performs correction processing described later; the IIR filter 161 performs filtering; and the data clipping section 162 clips off data including echo signal from a signal from the ultrasonic sensor 31 that performed signal reception. The phasing summation section 163 performs reception beamforming processing with phasing summation (delay and sum, DAS) using delay time data DD retrieved from the storage section 147. Subsequently, the wave detection section 165 performs full-wave rectification; the log compression section 166 performs compressed amplification; the dynamic range adjustment section 167 adjusts a dynamic range; the image plotting section 168 performs conversion to an image signal (luminance signal) for displaying an image on the display section 146. On the basis of the image signal, the control section 141 makes the display section 146 display an image showing a condition of a blood vessel. Processing for improving definition of an image by reception beamforming processing is not limited to a phasing summation, and another reception beamforming processing may be performed.

The storage section 147 in the console 140 stores cross talk amount data CD indicating a preset value as the amount of cross talk between the signal lines 41 in the FPC 40. The signal correction section 160 corrects the received electric signal RX1 output from the A/D converter 144, on the basis of cross talk amount data CD retrieved from the storage section 147.

The storage section 147 can store information of calibration for each of ultrasonic sensor arrays varying in configurations such as the frequency of ultrasound to be used and the number of ultrasonic sensors, and allow response to a plurality of ultrasonic sensor arrays. The storage section 147 is regardless of its aspects, and may be a storage medium fixed within an apparatus, such as an HDD or a solid storage medium (solid state drive, SSD), or a removable, portable storage medium to an apparatus.

Figure 11:
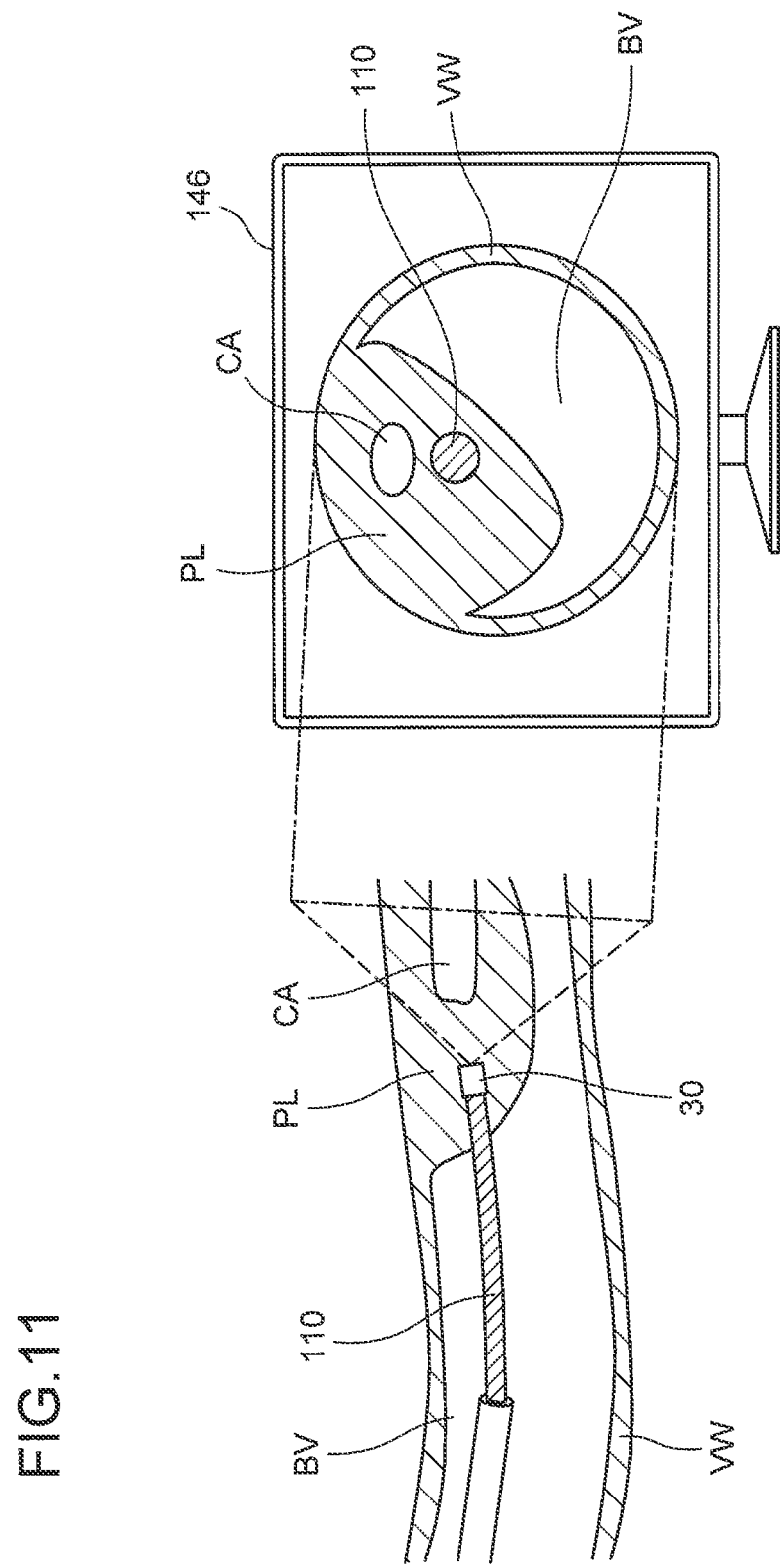
FIG. 11 is an explanatory diagram schematically illustrating a scene of displaying an image showing a condition of a blood vessel by the guide wire system 100.
Figure 12:
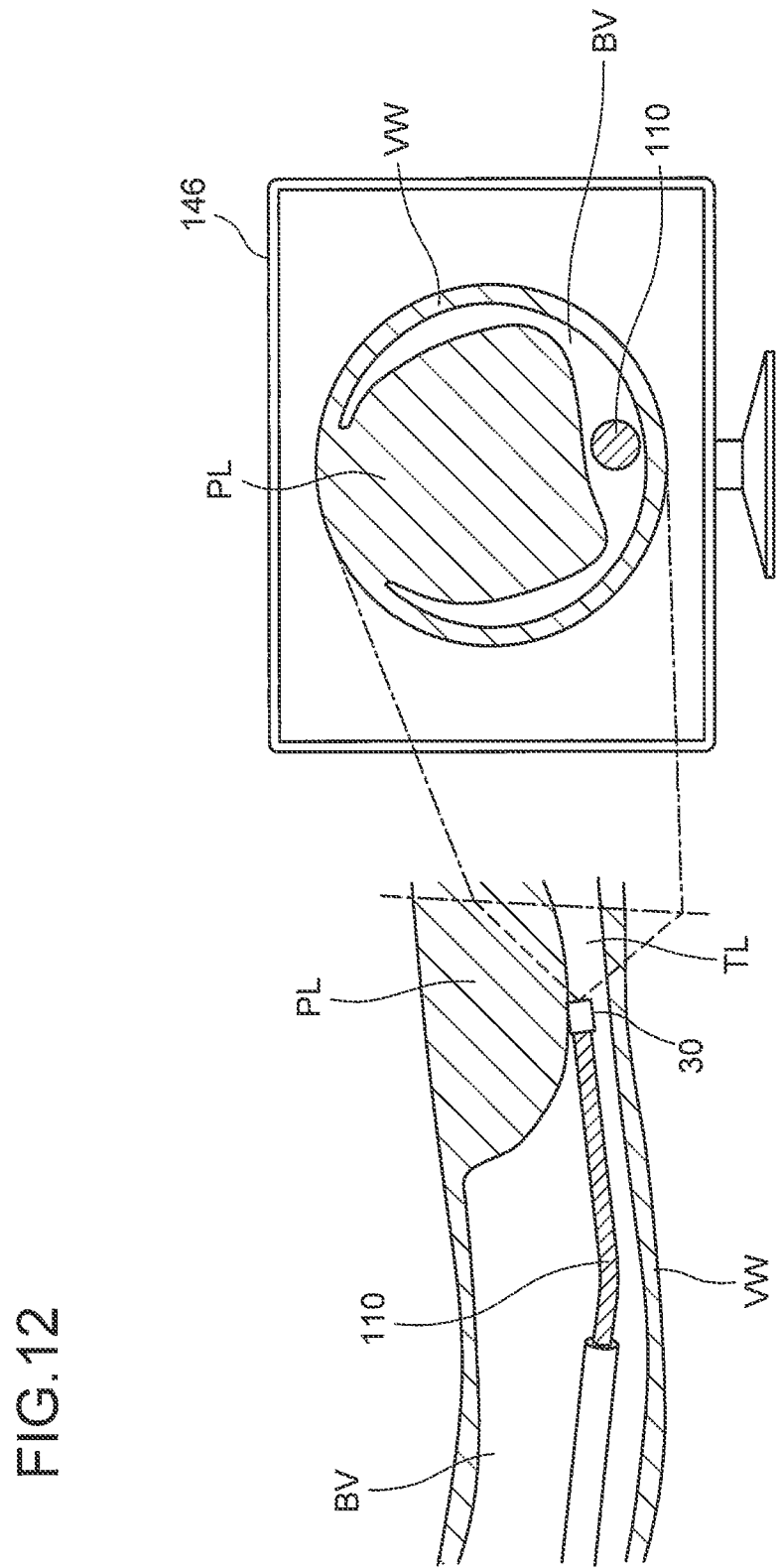
FIG. 12 is an explanatory diagram schematically illustrating a scene of displaying an image showing a condition of a blood vessel by the guide wire system 100.
Figure 13:
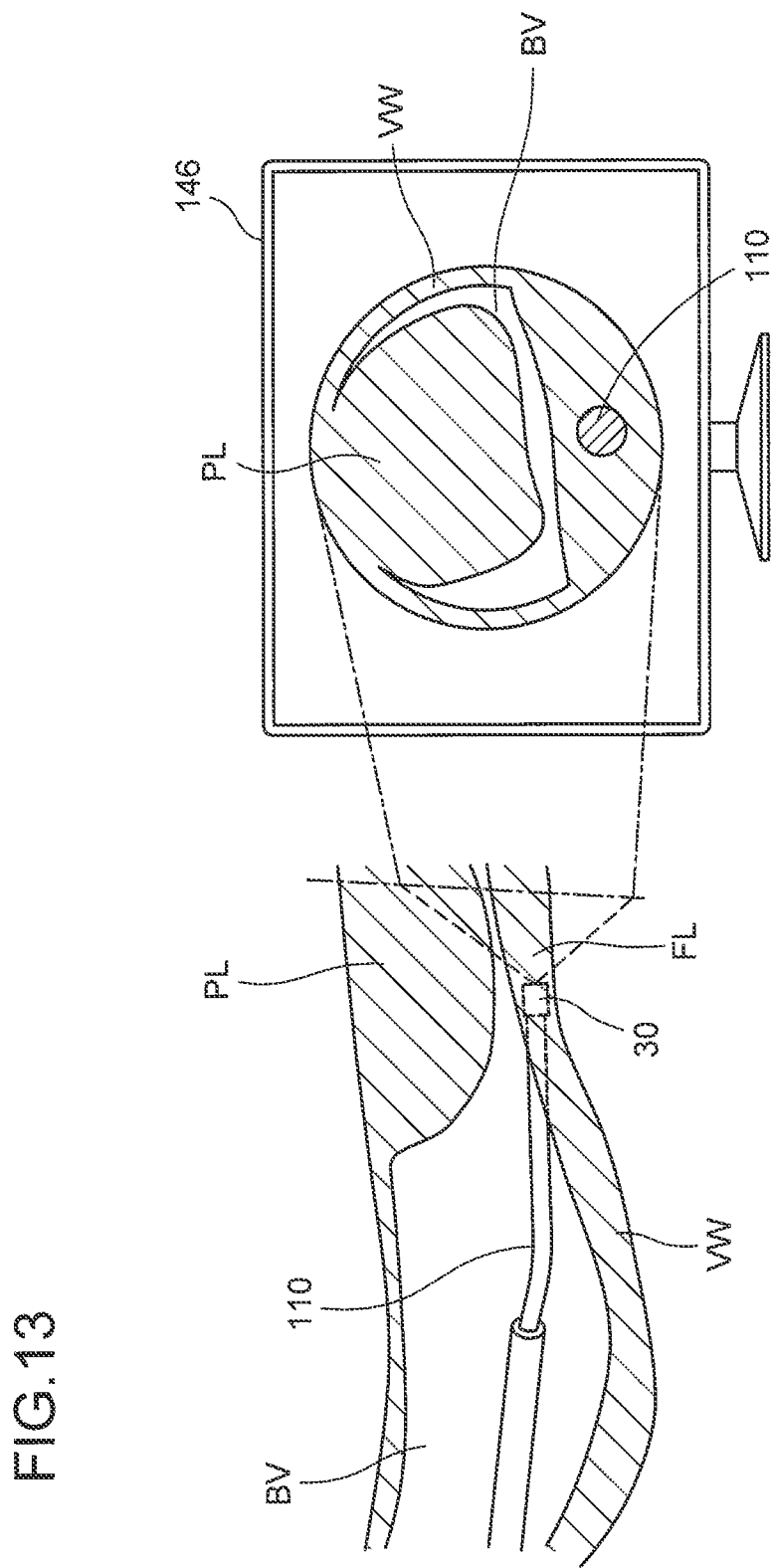
FIG. 13 is an explanatory diagram schematically illustrating a scene of displaying an image showing a condition of a blood vessel by the guide wire system 100.

FIG. 11-FIG. 13 are explanatory diagrams schematically illustrating scenes of displaying an image showing a condition of a blood vessel by the guide wire system 100 in the embodiment. FIG. 11-FIG. 13 depict scenes of displaying an image showing a condition of a blood vessel BV on the display section 146, by sending and receiving ultrasound by the ultrasonic sensor array 30 with inserting the guide wire 110 into the blood vessel BV.

For example, in the example of FIG. 11, the ultrasonic sensor array 30 placed at the distal end of the guide wire 110 burrows into a thrombus PL generated in the blood vessel BV, and the display section 146 displays an image showing a condition of a vascular wall VW of the blood vessel BV and a condition of the thrombus PL (including a condition of a cavitary CA within the thrombus PL). As such, the guide wire 110 in the embodiment has a smaller diameter relative to a catheter, thus allowing the ultrasonic sensor array 30 to easily burrow into the thrombus PL, and enabling identification of a condition of the inside of the thrombus PL. The guide wire 110 in the embodiment has a smaller diameter relative to a catheter, thus allowing the ultrasonic sensor array 30 to burrow into the thrombus PL and further pass through the thrombus PL, and enabling identification of a condition of the front of the thrombus PL.

For another example, in the example of FIG. 12, the ultrasonic sensor array 30 placed at the distal end of the guide wire 110 is located in a true lumen TL, which is in stenosis due to the thrombus PL generated in the blood vessel BV, and the display section 146 displays an image showing a condition of the vascular wall VW of the blood vessel BV and a condition of the thrombus PL. For another example, in the example of FIG. 13, the ultrasonic sensor array 30 placed at the distal end of the guide wire 110 is located within a false lumen FL of the vascular wall VW, and the display section 146 displays an image showing a condition of the vascular wall VW of the blood vessel BV and a condition of the thrombus PL. As such, the guide wire 110 in the embodiment has a smaller diameter relative to a catheter, thus allowing easy identification of entrance of the ultrasonic sensor array 30 to the false lumen FL rather than the true lumen TL, and enabling acquisition of information that contributes to subsequent appropriate operation of the guide wire 110.

Figure 14:
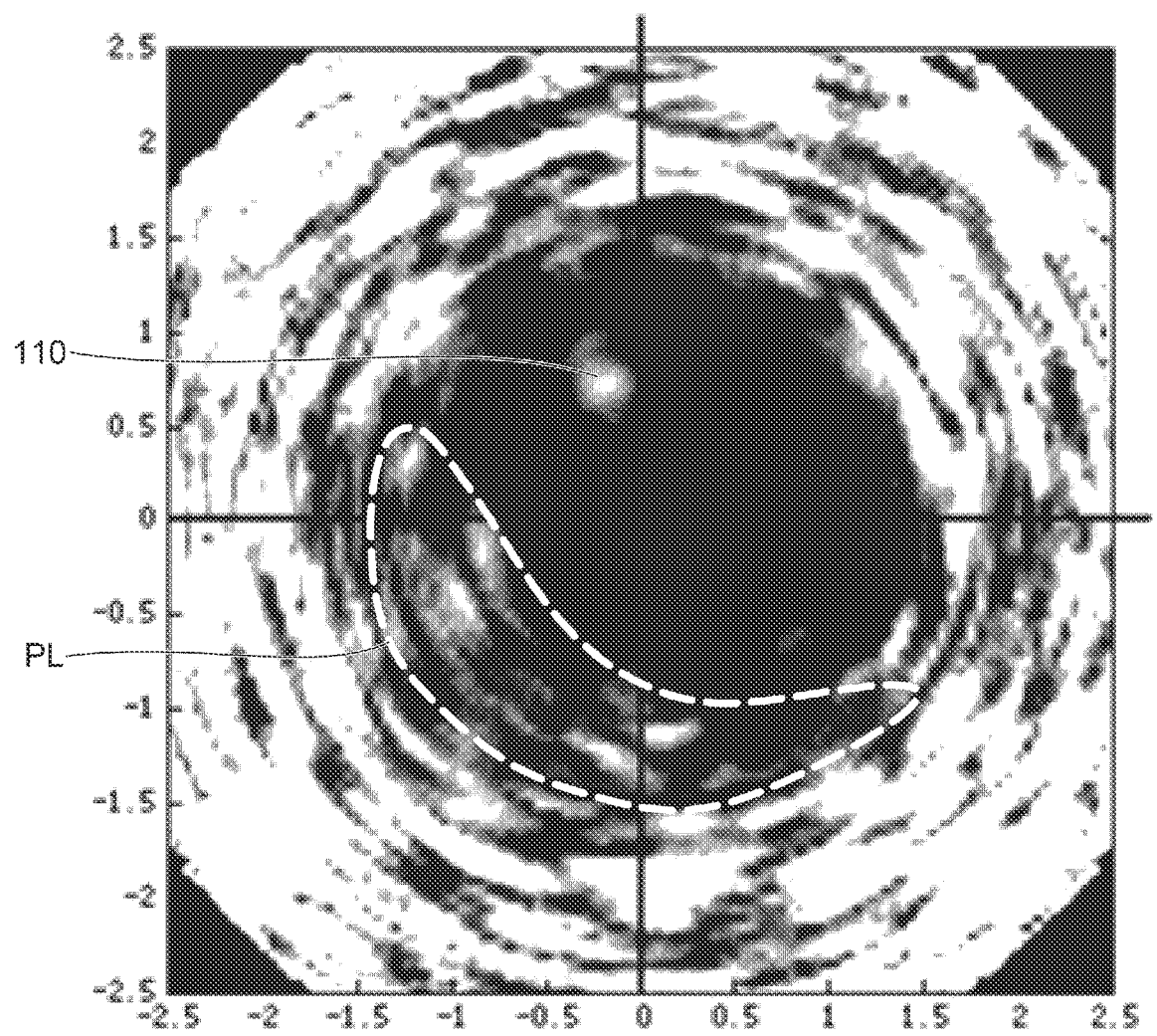
FIG. 14 is an explanatory diagram illustrating an example of images showing a condition of a blood vessel created by the guide wire system 100.
Figure 15:
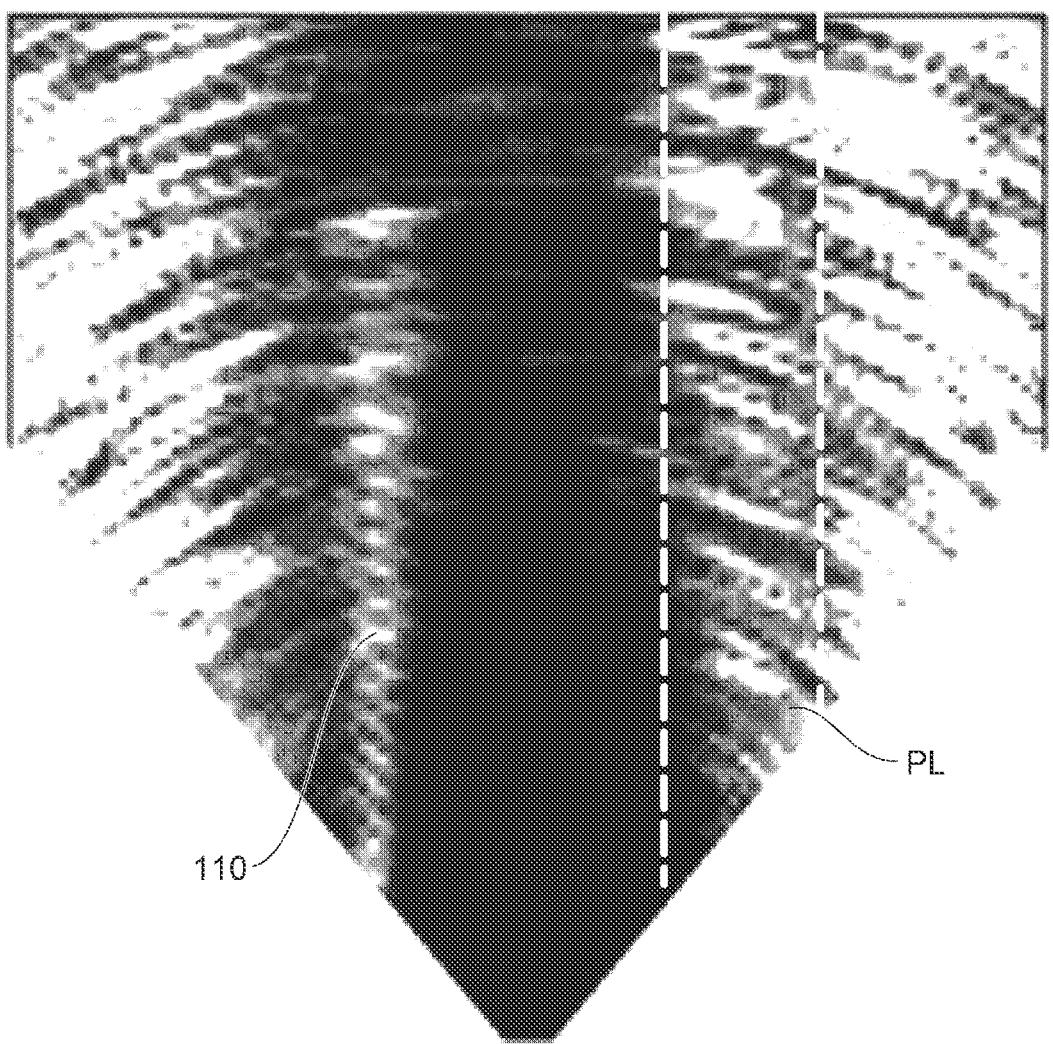
FIG. 15 is an explanatory diagram illustrating an example of images showing a condition of a blood vessel created by the guide wire system 100.

FIG. 14 and FIG. 15 are explanatory diagrams illustrating an example of images showing a condition of a blood vessel created by the guide wire system 100 in the embodiment. As shown in FIG. 14 and FIG. 15, the guide wire system 100 in the embodiment enables obtaining an image that accurately shows a condition of a blood vessel including a condition of the thrombus PL.

Figure 16:
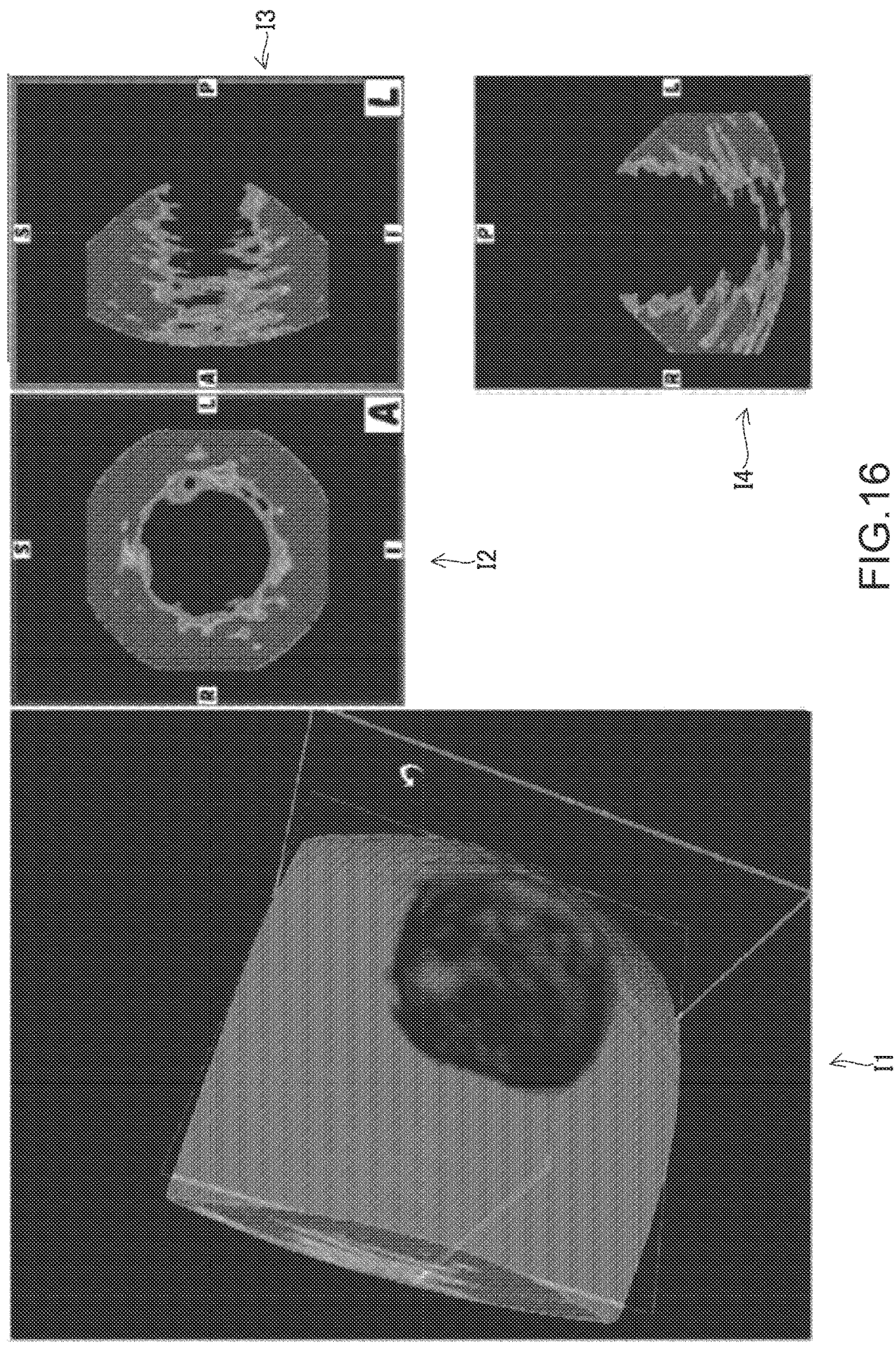
FIG. 16 shows explanatory diagrams illustrating an example of three-dimensional images showing a condition of a blood vessel created by the guide wire system 100.

In the embodiment, since a plurality of the ultrasonic sensors 31 configuring the ultrasonic sensor array 30 is placed two-dimensionally, it is also possible to obtain a three-dimensional image by volume rendering. FIG. 16 shows explanatory diagrams illustrating an example of three-dimensional images showing a condition of a blood vessel created by the guide wire system 100 in the embodiment. FIG. 16 depicts a three-dimensional image I1 showing a condition of a blood vessel, in addition to two-dimensional images I2-I4 showing conditions of the blood vessel.

A-3. Effect of the Embodiment

As described above, the ultrasonic sensor array 30 in the embodiment is a medical ultrasonic sensor array that includes a plurality of the ultrasonic sensors 31. The ultrasonic sensor array is formed by preparing a matrix material of an ultrasonic sensor made of an electrode layer to be the first electrode plate 33, an electrode layer to be the second electrode plate 34, and the piezoelectric element 32 sandwiched therebetween; cutting the piezoelectric element 32 from a side of the electrode layer to be the first electrode plate 33; and not cutting the electrode layer to be the second electrode plate 34 or partly cutting it through in a direction of thickness of the electrode layer.

In the conventional method of using a dicer to cut an ultrasonic sensor matrix material made of an electrode and a piezoelectric element to divide into individual ultrasonic sensors 31Y, and then arranging a plurality of the ultrasonic sensors 31Y in an array shape on a common substrate 300 (panel C of FIG. 3), when the ultrasonic sensor 31Y has a finely smaller size, it is difficult to make a regular arrangement on an X-Y plane where the plurality of the ultrasonic sensors 31Y is placed.

Panel A of FIG. 3 shows an exemplary diagram in which an electrode plate to be the second electrode plate 34 is partly cut through in a direction of thickness to form the ultrasonic sensor array 30. Each of the ultrasonic sensors 31 has the piezoelectric element 32, and the first electrode plate 33 and the second electrode plate 34 placed so as to sandwich the piezoelectric element 32. The first electrode plate 33 is separated for each of a plurality of the ultrasonic sensors 31. The second electrode plate 34 represents a single body of the second electrode plate 34 shared by the plurality of the ultrasonic sensors 31. The second electrode plate 34 is cut over at least a part in a direction of thickness from the surface 36 of a side having placement of each of the piezoelectric elements 32, at a position between a connection region to one of the piezoelectric element 32 (first piezoelectric element) and a connection region to another one of the piezoelectric elements 32 (second piezoelectric element) (see panel A of FIG. 3). Such method of formation leaves an uncut portion in at least a part in the direction of thickness of the second electrode plate 34 shared by a plurality of the ultrasonic sensors 31 configuring the ultrasonic sensor array 30. This enables prevention of a position gap within a X-Y plane where the plurality of the ultrasonic sensors 31 is placed, and allows prevention of signal reception delay.

The ultrasonic sensor array 30X in panel B of FIG. 3 is uncut on a surface 36X of a side having placement of each of the piezoelectric elements 32X in the second electrode plate 34X, unlike the ultrasonic sensor array 30 in panel A of FIG. 3. Such configuration enables prevention of a gap of a placement position of each of the ultrasonic sensors 31X within a X-Y plane, and allows prevention of signal reception delay.

The ultrasonic sensor array 30 in panel A of FIG. 3 has a cut on the surface 36 of the side having placement of each of the piezoelectric element 32 in the second electrode plate 34. As indicated by arrows in panel A of FIG. 3, the ultrasonic sensor array 30 thus enables prevention of vibration of the piezoelectric element 32 of a certain one of the ultrasonic sensors 31 from transmitting in an arrangement direction of the ultrasonic sensors 31 via the second electrode plate 34. Consequently, in addition to prevention of signal reception delay due to prevention of a position gap within an arrangement plane X-Y of a plurality of the ultrasonic sensors 31, it is possible to further prevent generation of mechanical cross talk that generates in the piezoelectric element 32 of another adjacent of the ultrasonic sensors 31.

The guide wire 110 in the embodiment includes the guide wire body 112, and the ultrasonic sensor array 30 placed at the distal end part of the guide wire body 112. The ultrasonic sensor array 30 is placed such that an ultrasonic sender-receiver face of each of the ultrasonic sensors 31 directs forward in a direction of insertion of the guide wire body 112. As such, the guide wire 110 in the embodiment has the ultrasonic sensor array 30 placed at the distal end part of the guide wire body 112 in a forward viewing manner in a guide wire having a relatively small diameter, thus allows the ultrasonic sensor array 30 to easily burrow into the thrombus PL, and enables achievement to obtain high-definition image information of the inside of the thrombus PL with use of an ultrasonic sensor array.

In the guide wire 110 in the embodiment, the guide wire body 112 includes the core shaft 10, which is made of metal, and the second electrode plate 34 of the ultrasonic sensor array 30 is electrically connected to the core shaft 10. The guide wire 110 in the embodiment thus enables use of the core shaft 10 as a standard potential line (e.g., a GND potential line) electrically connected to a plurality of the ultrasonic sensors 31, and allows achievement to simplify a configuration of an apparatus.

The guide wire 110 in the embodiment further includes the electrode terminal portion 70 placed at the proximal end part of the guide wire body 112, and the FPC 40 as a signal transmission portion that transmits a signal between the first electrode plate 33 of each of a plurality of the ultrasonic sensors 31 and the electrode terminal portion 70. The FPC 40 includes the signal line 41 individually disposed for each of the plurality of the ultrasonic sensors 31. Each of the signal lines 41 transmits a sent electric signal to be input to the ultrasonic sensor 31 for sending of ultrasound, from an electrode terminal portion 70 to the ultrasonic sensor 31, and also transmits a received electric signal output from the ultrasonic sensor 31 corresponding to received ultrasound, from the ultrasonic sensor 31 to the electrode terminal portion 70. In this manner, the guide wire 110 in the embodiment enables achievement of signal transmission between the electrode terminal portion 70 and the ultrasonic sensor 31 without using an IC or the like that controls signal transmission for each of the ultrasonic sensors 31, thus allowing avoidance of limited voltage value associated with use of an IC or the like, and providing avoidance of shallower exploration depth of each of the ultrasonic sensors 31 due to the limited voltage value.

In the guide wire 110 in the embodiment, the FPC 40 includes a constant-voltage wiring 42 placed between one signal line 41A disposed for one of the ultrasonic sensors 31, and another signal line 41B disposed for another of the ultrasonic sensors 31. The guide wire 110 in the embodiment thus has difficulty to employ a coaxial cable because of need of a relatively small diameter and also flexibility to be bendable along a blood vessel. Moreover, if signal deterioration due to electrical cross talk occurs in obtaining an image, it will cause reduction in definition of the image. A configuration including the constant-voltage wiring 42 between one signal line 41A and another signal line 41B enables prevention of occurrence of deterioration of a signal due to electrical cross talk between one signal line 41A disposed for one of the ultrasonic sensors 31 and another signal line 41B disposed for another of the ultrasonic sensors 31 even in installation of a plurality of the signal lines 41, and allows achievement to obtain higher-definition image information of the blood vessel with use of the ultrasonic sensor array.

The guide wire system 100 in the embodiment includes the guide wire 110 and the control apparatus 150. The control apparatus 150 has the connector 120 as a connection terminal portion electrically connected to the electrode terminal portion 70 of the guide wire 110, and controls the signal transmission. The control apparatus 150 (the console 140, which configures the control apparatus 150) also includes the control section 141 that makes the display section 146 display an image showing a condition of a blood vessel on the basis of a received electric signal output from each of the ultrasonic sensors 31. The guide wire system 100 in the embodiment thus enables achievement to display a high-definition image showing a condition of a blood vessel (e.g., a condition of the thrombus PL) with use of the ultrasonic sensor array.

In the guide wire system 100 in the embodiment, the control apparatus 150 (the PIM 130, which configures the control apparatus 150) has the end terminal resistance circuit X, the first switching circuit SW1, and the second switching circuit SW2. The first switching circuit SW1 successively selects one received electric signal among received electric signals received respectively from the signal lines 41 connected via the electrode terminal portion 70 and the connector 120, and sends it to the control section 141. The second switching circuit SW2 selects each of received electric signals unselected by the first switching circuit SW1, among the received electric signals received respectively from the signal lines 41 connected via the electrode terminal portion 70 and the connector 120, and sends it to the end terminal resistance circuit X. Thus, in the guide wire system 100 in the embodiment, prevention of generation of reflection of a signal at the end terminal part of the signal line 41 enables effective prevention of generation of signal distortion due to signal reflection at the terminal part of the signal line 41 even in installation of a plurality of the signal lines 41, and allows achievement to obtain higher-definition image information with use of the ultrasonic sensor array.

In the guide wire system 100 in the embodiment, the control section 141 of the console 140 includes a signal correction section 160. The signal correction section 160 corrects a received electric signal transmitted by one of the signal lines 41 on the basis of a value preset as the amount of electrical cross talk between one signal line 41A disposed for one of the ultrasonic sensors 31 and another signal line 41B disposed for another of the ultrasonic sensors 31. Accordingly, the guide wire system 100 in the embodiment identifies the static emission of electrical cross talk between the signal lines 41 and corrects the received electric signal, thereby enabling mitigation of effect of the electrical cross talk, and allowing achievement to obtain high-definition image information with use of the ultrasonic sensor array.

A-4. Modifies Example of First Embodiment

Figure 17:
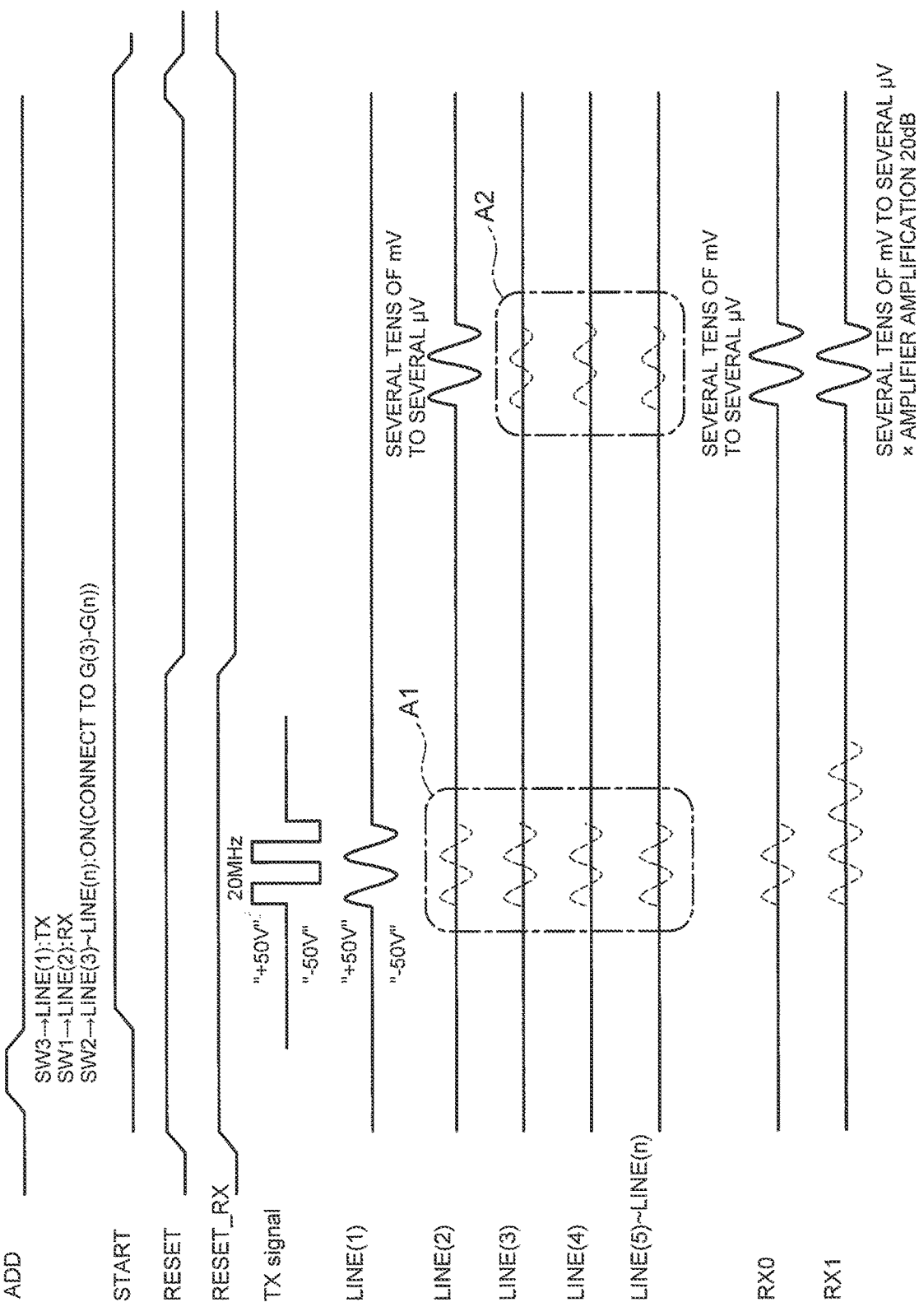
FIG. 17 is a timing chart illustrating an example of actions of a PIM 130 in a modified example of the first embodiment.

FIG. 17 is a timing chart illustrating an example of actions of the PIM 130 in a modified example of the first embodiment. Compared to the first embodiment shown in FIG. 9, the modified example shown in FIG. 17 is different in that at the same timing as the timing of switching of RESET_RX signal from level H to level L, RESET signal is also switched from level H to level L. The modified example shown in FIG. 17 has an aspect in which a signal line LINE selected for sending (LINE(1) in the example of FIG. 17) is connected to the TX driver 131 via the third switching circuit SW3; in which a signal line LINE selected for reception (LINE(2)) is connected to the protective circuit 132 and the preamplifier 133 via the first switching circuit SW1; and in which unselected signal lines LINE (LINE(3)-LINE(n)) are connected to any of the end terminal resistances Rg; the aspect performs their control by RESET signal. An action in accordance with the timing chart of the modified example shown in FIG. 17 also enables prevention of generation of electrical cross talk by switching actions of the switching circuits SW1-SW3, as with the first embodiment shown in FIG. 9.

B. SECOND EMBODIMENT

Figure 18:
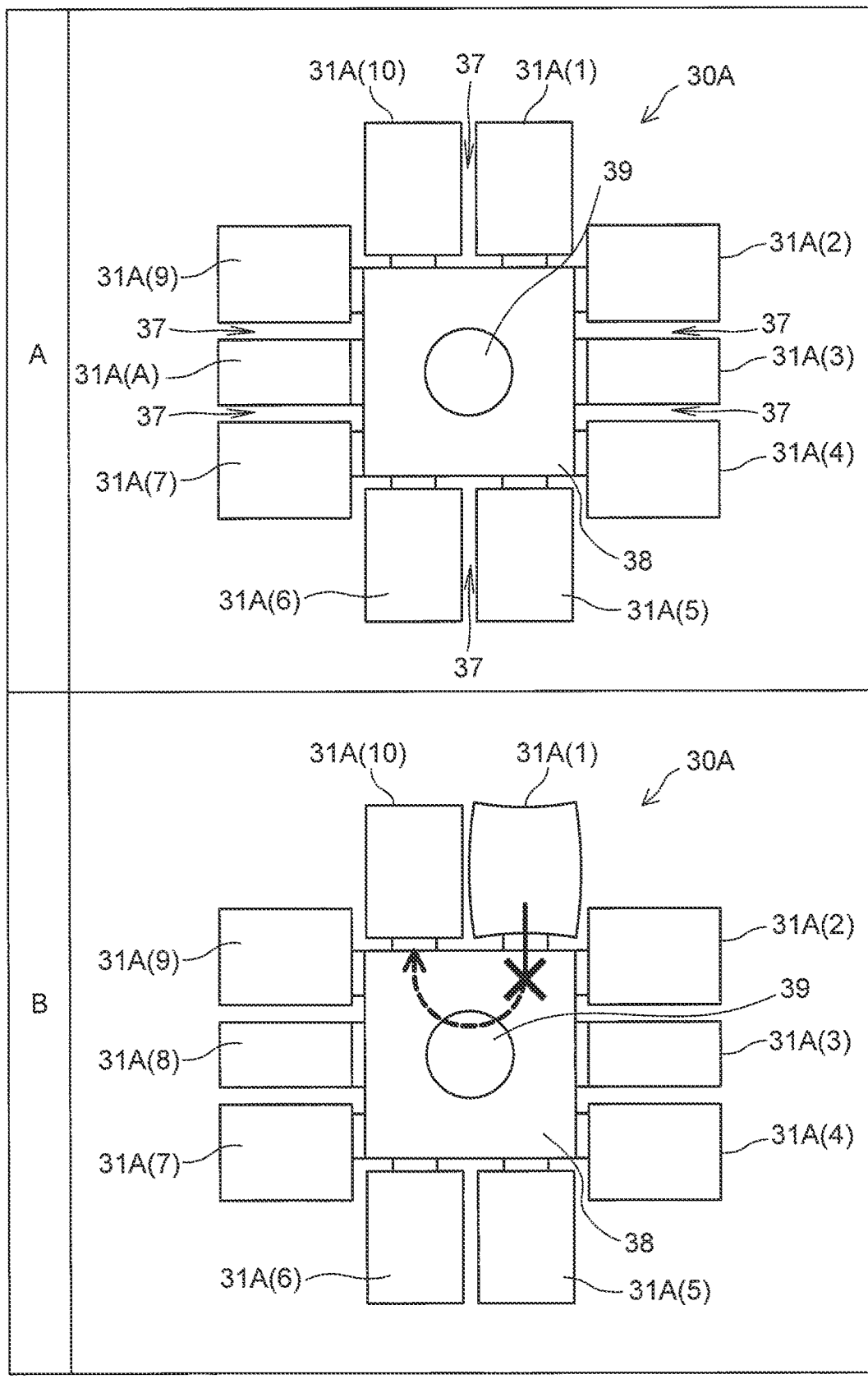
FIG. 18 shows explanatory diagrams schematically illustrating a configuration of an ultrasonic sensor array 30 in a second embodiment.

FIG. 18 shows explanatory diagrams schematically illustrating a configuration of an ultrasonic sensor array 30A in a second embodiment. Hereinafter, description will be appropriately omitted for the same configuration as in the ultrasonic sensor array 30 in the first embodiment described above among configurations of the ultrasonic sensor array 30A in the second embodiment, by providing the same symbols.

As shown in panel A of FIG. 18, the ultrasonic sensor array 30A in the second embodiment includes a plurality of (10) ultrasonic sensors 31A (31A(1)-31A(10)) arranged two-dimensionally. The plurality of ultrasonic sensors 31A is circularly placed in planar view. In other words, the ultrasonic sensor array 30A in the second embodiment has an annular-type array structure.

The ultrasonic sensor array 30A also has a non-oscillatory part 38 placed at a position surrounded by the plurality of ultrasonic sensors 31A. The non-oscillatory part 38 has a piezoelectric element 32, and a first electrode plate 33 and a second electrode plate 34 that sandwich the piezoelectric element 32, as similar to the ultrasonic sensor 31A. The second electrode plate 34 of the non-oscillatory part 38 is a member integrated with the second electrode plate 34 of each of the ultrasonic sensors 31A. In other words, a single body of the second electrode plate is shared by each of the ultrasonic sensors 31A and the non-oscillatory part 38.

The non-oscillatory part 38 has a feedthrough via 39 that conducts the first electrode plate 33 to the second electrode plate 34. The first electrode plate 33 of the non-oscillatory part 38 thus has constantly the same potential as the second electrode plate 34 (e.g., 0 V). This caused the non-oscillatory part 38 to keep prevention of vibration of the piezoelectric element 32. A single body of the second electrode plate 34 shared by each of the ultrasonic sensors 31A and the non-oscillatory part 38 is cut over the whole in a direction of thickness from the surface having each of the piezoelectric elements 32 placed, at a position between a connection region to one of the piezoelectric elements 32 (first piezoelectric element) and a connection region to another one of the piezoelectric elements 32 (second piezoelectric element). That is, in each position 37 in panel A of FIG. 18, the second electrode plate 34 is cut over the whole in a direction of thickness.

In this manner, the ultrasonic sensor array 30A in the second embodiment has the non-oscillatory part 38, which is placed at a position surrounded by a plurality of the ultrasonic sensors 31A and shares the second electrode plate 34. The second electrode plate 34 is cut over the whole in a direction of thickness from the surface having each of the piezoelectric elements 32 placed, at the position 37 between a connection region to one of the piezoelectric elements 32 (first piezoelectric element) and a connection region to another one of the piezoelectric elements 32 (second piezoelectric element). Accordingly, as shown in panel B of FIG. 18, even when the piezoelectric element 32 of one of the ultrasonic sensors 31A (ultrasonic sensor 31A(1)) vibrates, the vibration is not directly conveyed to another of the ultrasonic sensors 31A but conveyed to the non-oscillatory part 38, and attenuates at the non-oscillatory part 38, thus enabling prevention of the vibration from transmitting to the piezoelectric element 32 of another of the ultrasonic sensors 31A, and consequently allowing effective prevention of generation of mechanical cross talk in which the piezoelectric element 32 of another of the ultrasonic sensors 31A also vibrates.

C. THIRD EMBODIMENT

Figure 19:
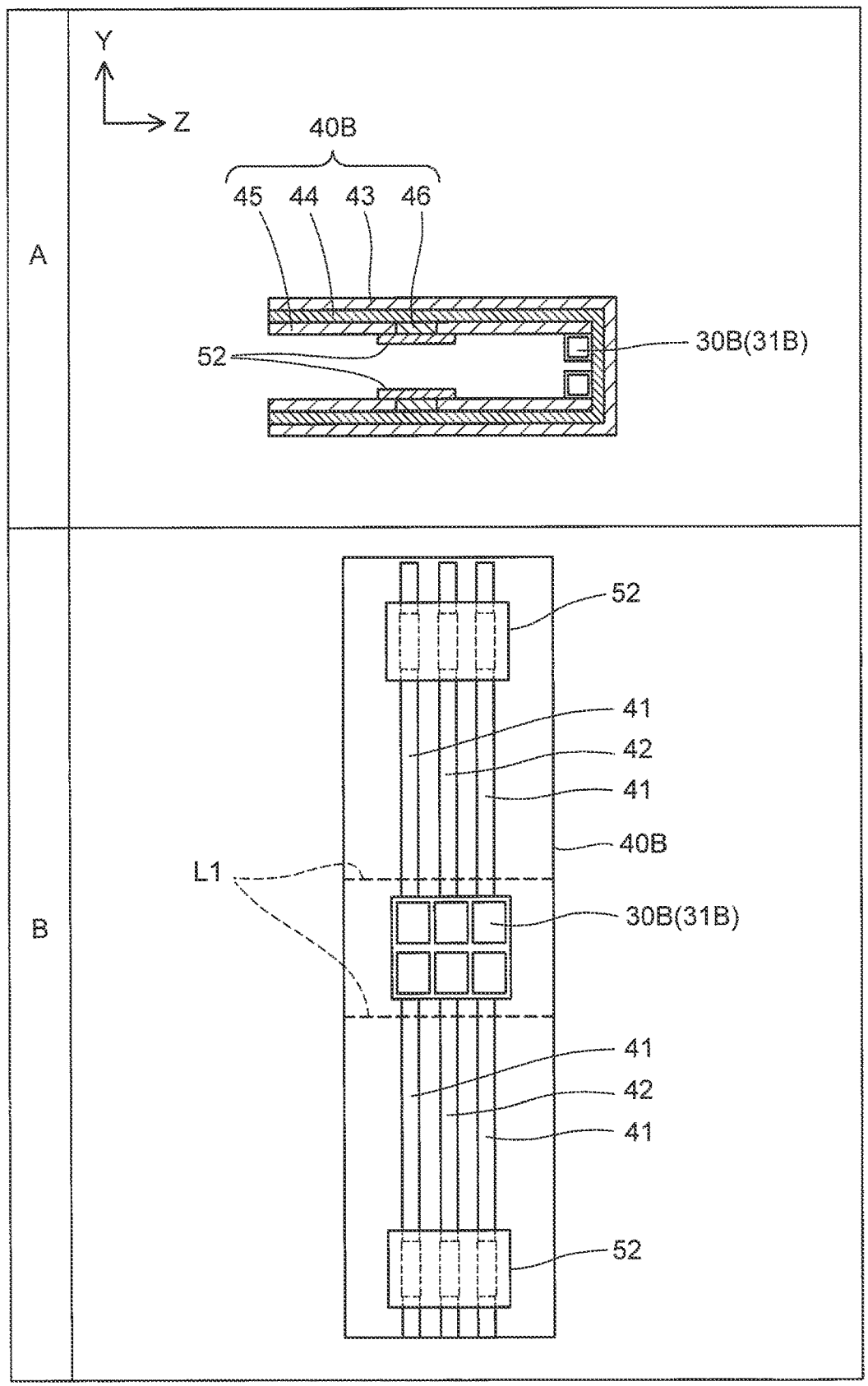
FIG. 19 shows explanatory diagrams schematically illustrating a configuration of a peripheral part of an ultrasonic sensor array 30 and an FPC 40 in a guide wire 110 in a third embodiment.

FIG. 19 shows explanatory diagrams schematically illustrating a configuration of a peripheral part of an ultrasonic sensor array 30B and an FPC 40B in a guide wire 110 in a third embodiment. Panel A of FIG. 19 shows a configuration of a cross section in a state where the FPC 40B is folded at a fold line L1 (YZ cross section), and panel B of FIG. 19 shows a configuration of a plane in a state of developing the FPC 40B. Hereinafter, description will be appropriately omitted for the same configuration as in the first embodiment described above among configurations of the peripheral part of the ultrasonic sensor array 30B and the FPC 40B in the third embodiment, by providing the same symbols.

As shown in panel A and panel B of FIG. 19, on the FPC 40B in the third embodiment, a matching resistance 52 that adjusts impedance is disposed at a site of connection of each of the ultrasonic sensors 31B configuring the ultrasonic sensor array 30B, to each of signal lines 41 of the FPC 40B. The connection site generates change of impedance, and thus produces reflection of a signal. The matching resistance 52 is disposed in order to prevent such reflection of a signal from deteriorating a signal that runs in each of the signal lines 41. More specifically, the FPC 40B is configured of a base layer 43, a wiring layer 44, and a cover layer 45; an electrically-conductive pad 46 is disposed which connects to each of the signal lines 41 and a constant-voltage wiring 42 in the wiring layer 44; and the matching resistance 52 is connected so as to extend over the electrically-conductive pads 46 disposed on the signal lines 41, and the electrically-conductive pad 46 disposed on the constant-voltage wiring 42.

In this manner, the guide wire 110 in the third embodiment includes the matching resistance 52, which adjusts impedance between each of the ultrasonic sensors 31B and the signal lines 41. This enables prevention of generation of signal reflection at a connection point of each of the ultrasonic sensors 31B and the signal lines 41. Particularly, in the ultrasonic sensor array 30B having a relatively small size for installing in the guide wire 110 having a relatively a small diameter, signal deterioration due to such signal reflection has a greater effect when a higher frequency of ultrasound sent from the ultrasonic sensor 31B is provided for improving resolution; however, the guide wire 110 in the third embodiment enables prevention of generation of such signal reflection.

Figure 20:
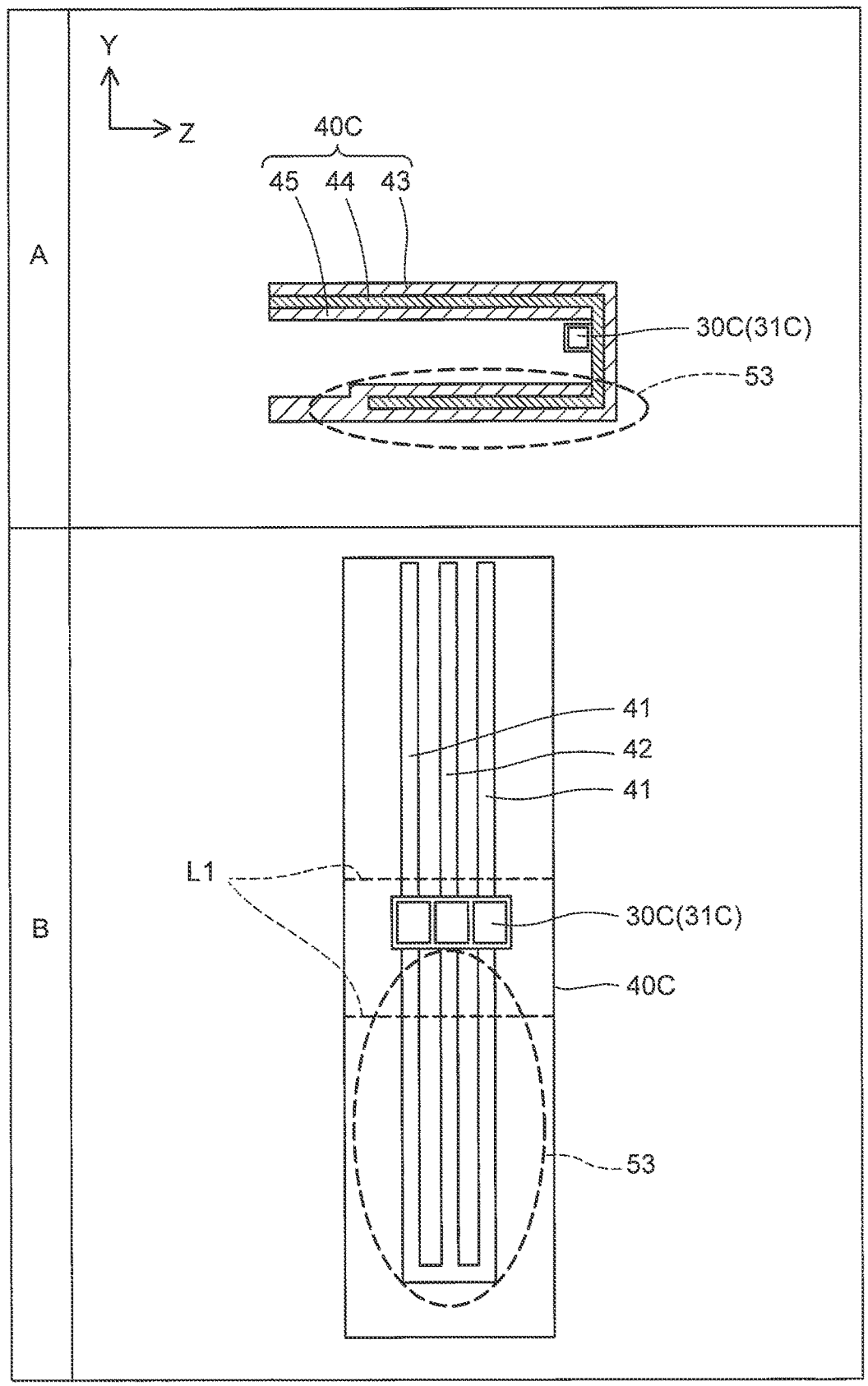
FIG. 20 shows explanatory diagrams schematically illustrating a configuration of a peripheral part of an ultrasonic sensor array 30 and a FPC 40 in a guide wire 110 in a first modified example of the third embodiment.

FIG. 20 shows explanatory diagrams schematically illustrating a configuration of a peripheral part of an ultrasonic sensor array 30C and a FPC 40C in a guide wire 110 in a first modified example of the third embodiment. In the first modified example of the third embodiment shown in FIG. 20, instead of the matching resistance 52 in the third embodiment shown in FIG. 19, a matching resistance 53 is configured by sheet resistance of a wiring layer 44 itself of the FPC 40C. That is, in the wiring layer 44 of the FPC 40C, a part connected to each of ultrasonic sensors 31C configuring the ultrasonic sensor array 30C is additionally disposed separately from signal lines 41 and a constant-voltage wiring 42, and such part is set as the matching resistance 53. The first modified example of the third embodiment also includes the matching resistance 53, which adjusts impedance between each of the ultrasonic sensors 31C and the signal lines 41, thus enabling prevention of generation of signal reflection at a connection point of each of the ultrasonic sensors 31C and the signal lines 41.

Figure 21:
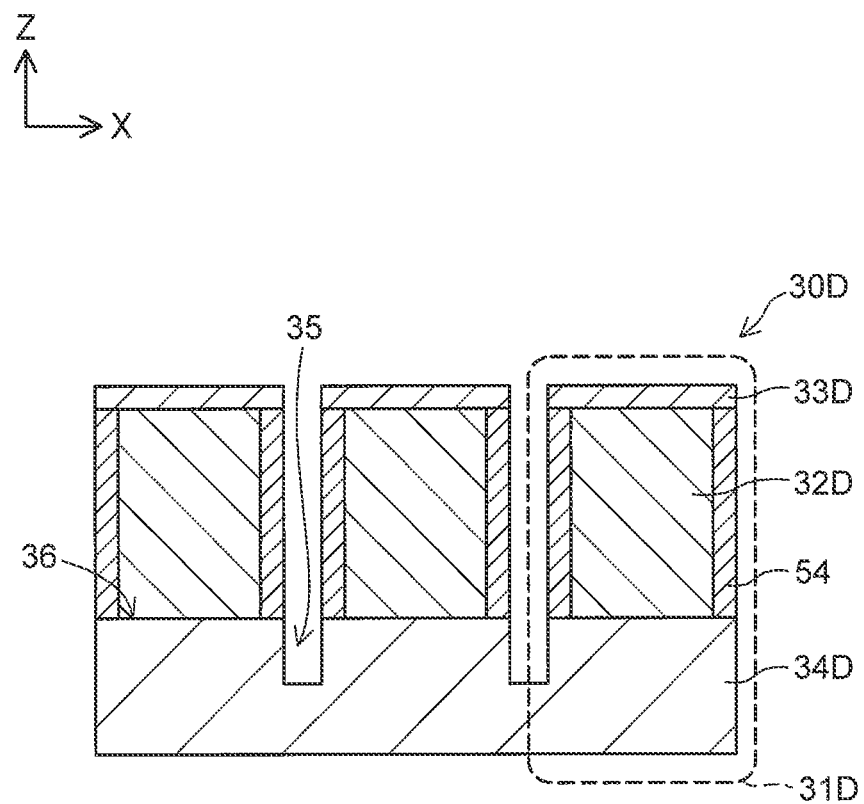
FIG. 21 shows explanatory diagrams schematically illustrating a configuration of an ultrasonic sensor array 30 in a guide wire 110 in a second modified example of the third embodiment.

FIG. 21 shows explanatory diagrams schematically illustrating a configuration of an ultrasonic sensor array 30D in a guide wire 110 in a second modified example of the third embodiment. In the second modified example of the third embodiment shown in FIG. 21, instead of the matching resistance 52 in third embodiment shown in the FIG. 19, a matching resistance 54 that connects a first electrode plate 33D to a second electrode plate 34D is disposed in each of ultrasonic sensors 31D configuring the ultrasonic sensor array 30D. Such matching resistance 54 may, for example, be formed by melting a wall surface of a piezoelectric element 32D with a laser, or by forming a resistance element as a film by vapor deposition, epitaxial growth, or the like. The second modified example of the third embodiment also includes the matching resistance 54, which adjusts impedance between each of the ultrasonic sensors 31D and the signal lines 41, thus enabling prevention of generation of signal reflection at a connection point of each of the ultrasonic sensors 31D and the signal lines 41.

D. FOURTH EMBODIMENT

Figure 22:
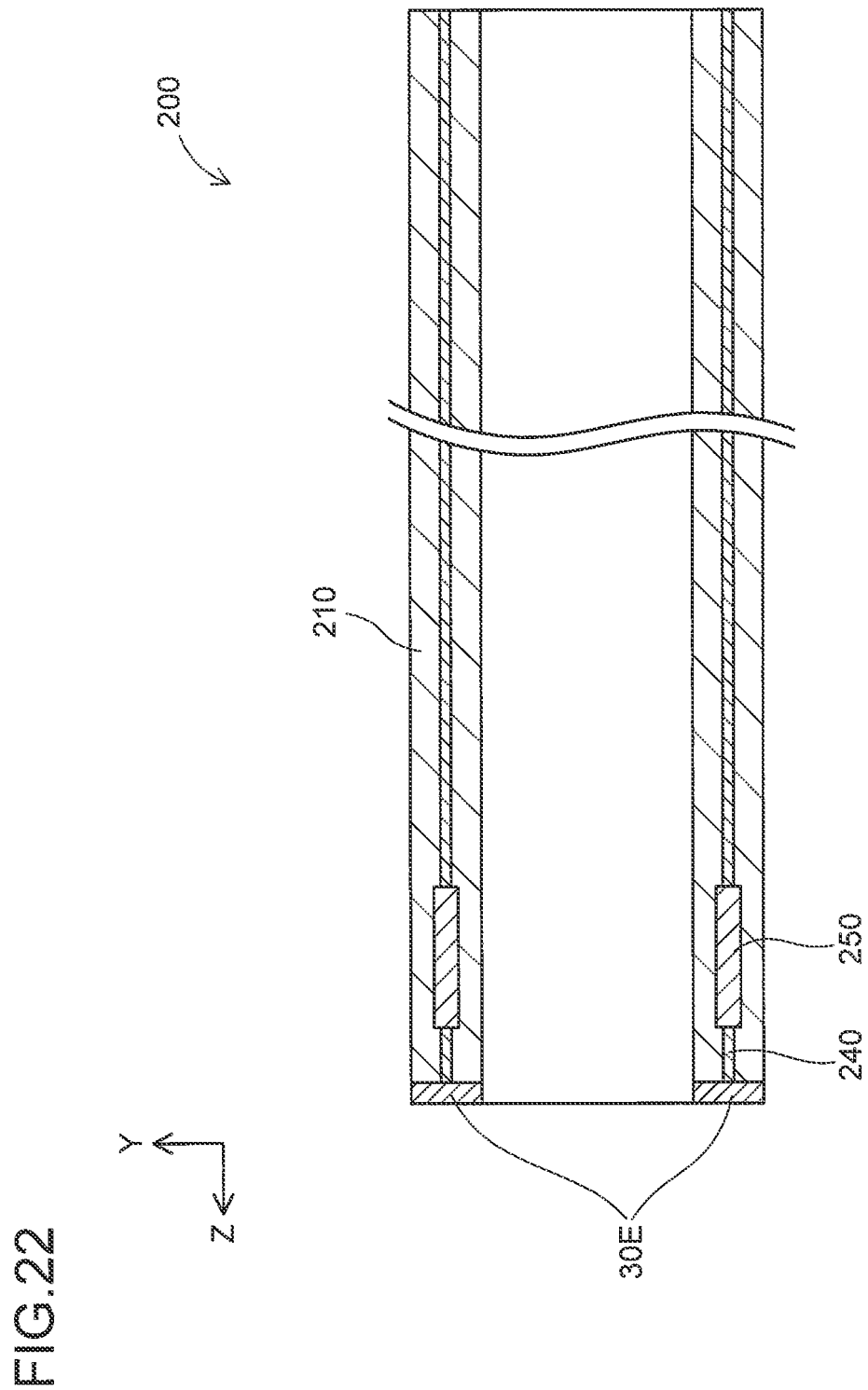
FIG. 22 is an explanatory diagram schematically illustrating a configuration of a catheter 200 in a fourth embodiment.

FIG. 22 is an explanatory diagram schematically illustrating a configuration of a catheter 200 in a fourth embodiment. The fourth embodiment is an embodiment where the ultrasonic sensor array 30 in the first embodiment is installed in a catheter 200 rather than the guide wire 110.

As shown in FIG. 22, the catheter 200 includes a catheter body 210, and an ultrasonic sensor array 30E placed at the distal end part of the catheter body 210. A configuration of the ultrasonic sensor array 30E installed in the catheter body 210 is similar to the configuration of the ultrasonic sensor array 30 installed in the guide wire 110 in first embodiment. The ultrasonic sensor array 30E is placed such that an ultrasonic sender-receiver face of each of the ultrasonic sensors 31 directs forward in a direction of insertion of the catheter body 210. The catheter 200 in the embodiment includes an IC 250 connected to the ultrasonic sensor array 30E via a signal line 240, and the IC 250 controls sending and reception of ultrasound in the ultrasonic sensor array 30E. The ultrasonic sensor array 30E, which is included in the catheter 200 in the fourth embodiment, has a configuration similar to that of the ultrasonic sensor array 30 in first embodiment, and thus enables prevention of generation of mechanical cross talk between the ultrasonic sensors 31.

A configuration may be employed in which the catheter body 210 includes a metallic reinforcing body not depicted, and in which a second electrode plate 34 of the ultrasonic sensor array 30E is electrically connected to the reinforcing body. Employment of such configuration enables use of a reinforcing body as a standard potential line (e.g., a GND potential line) electrically connected to a plurality of the ultrasonic sensors 31, and allows achievement to simplify a configuration of an apparatus.

E. MODIFIED EXAMPLES

The technology disclosed herein is not limited to the embodiments described above, and can be modified to a variety of aspects within the range not departing from its spirits; for example, the following modification is also available.

The configuration of the ultrasonic sensor array 30 in the embodiment is thoroughly an example, and can be modified variously. For example, although the first embodiment described above employs a configuration where the second electrode plate 34 is cut over a part in a direction of thickness at every position between a connection region to a certain one of the piezoelectric elements 32 and a connection region to another of the piezoelectric elements 32 in the ultrasonic sensor array 30, such configuration (a configuration where the second electrode plate 34 is cut over a part in a direction of thickness) may be employed only in a part of the above-mentioned position in the ultrasonic sensor array 30.

Although in the first embodiment described above, the second electrode plate 34 shared by a plurality of the ultrasonic sensors 31 configuring the ultrasonic sensor array 30 is cut over a part in a direction of thickness from the surface 36 having each of the piezoelectric elements 32 placed, at a position between a connection region to a certain one of the piezoelectric elements 32 and a connection region to another of the piezoelectric elements 32, the second electrode plate 34 may be cut over the whole in a direction of thickness from the surface 36 at such position as long as the second electrode plate 34 is shared by the plurality of the ultrasonic sensors 31.

Although in the embodiment described above, a second electrode plate 34 is shared by all of the ultrasonic sensors 31 configuring the ultrasonic sensor array 30, the second electrode plate 34 may be shared by only some of the ultrasonic sensors 31 configuring the ultrasonic sensor array 30 (i.e., a plurality of the ultrasonic sensors 31). In such case, it is only necessary to dispose another second electrode plate 34 for other some of the ultrasonic sensors 31 configuring the ultrasonic sensor array 30.

In the embodiment described above, the number or arrangement of the ultrasonic sensors 31 configuring the ultrasonic sensor array 30 is thoroughly an example, and can be modified variously. For example, although in the embodiment described above, a plurality of the ultrasonic sensors 31 configuring the ultrasonic sensor array 30 is arranged two-dimensionally, the plurality of the ultrasonic sensors 31 may be arranged one-dimensionally (in a line). Although in the embodiment described above, a ultrasonic sender-receiver face of each of the ultrasonic sensors 31 configuring the ultrasonic sensor array 30 is placed so as to direct forward in a direction of insertion of the guide wire body 112 (or the catheter body 210), the ultrasonic sender-receiver face of each of the ultrasonic sensor 31 may be placed so as to direct in another direction (e.g., a radial direction of the guide wire body 112 or the catheter body 210). Although in the embodiment described above, the second electrode plate 34 of the ultrasonic sensor array 30 is electrically connected to the core shaft 10 or a reinforcing body, such configuration is not always necessary.

The configuration of the guide wire 110 and the catheter 200 in the embodiment described above is thoroughly an example, and can be modified variously. For example, although in the embodiment described above, the core shaft 10 of the guide wire 110 is configured of the small-diameter portion 11, the tapered portion 12, and the large-diameter portion 13, the core shaft 10 may not have at least one of these three portions, or may have another portion in addition to the three portions. Component materials formed of one part and another part of the core shaft 10 may be different from each other. In the embodiment described above, a part of a configuration of the guide wire 110 or the catheter 200 may be omitted. For example, although in the embodiment described above, the guide wire 110 includes the outer shaft 80, the guide wire 110 may not have the outer shaft 80.

In the embodiment described above, a configuration of the control apparatus 150 is thoroughly an example, and can be modified variously. For example, in the embodiment described above, a configuration included in the PIM 130 may be included in the console 140 rather than the PIM 130, or conversely, a configuration included in the console 140 may be included in the PIM 130 rather than the console 140. A part of a configuration included in the PIM 130 or the console 140 may be omitted. The control apparatus 150 may be a single apparatus rather than separated into the PIM 130 and the console 140, or may include an apparatus other than the PIM 130 and the console 140. In each of the embodiments described above, a part of a configuration achieved by hardware may be replaced with software, or conversely, a part of a configuration achieved by software may be replaced with hardware. The method of drive and control of the ultrasonic sensor array 30 in the embodiment described above is thoroughly an example, and can be modified variously.

The production method of the ultrasonic sensor array 30 in the embodiment described above is thoroughly an example, and can be modified variously.

DESCRIPTION OF REFERENCE NUMERALS

10: core shaft
11: small-diameter portion
12: tapered portion
13: large-diameter portion
18: resin coat layer
19: solder material
22: coil body
30: ultrasonic sensor array
31: ultrasonic sensor
32: piezoelectric element
33: first electrode plate
34: second electrode plate
35: cavity
36: surface
37: position
38: non-oscillatory part
39: feedthrough via
40: FPC
41: signal line
42: constant-voltage wiring
43: base layer
44: wiring layer
45: cover layer
46: electrically-conductive pad
50: housing
52: matching resistance
53: matching resistance
54: matching resistance
60: backing material
70: electrode terminal portion
72: electrode ring
80: outer shaft
90: insulative resin
100: guide wire system
110: guide wire
112: guide wire body
120: connector
122, 124: cable
130: PIM
131: TX driver
132: protective circuit
133: preamplifier
140: console
141: control section
143: sequence control circuit
144: A/D converter
145: operation section
146: display section
147: storage section
148: bus
150: control apparatus
160: signal correction section
161: IIR filter
162: data clipping section
163: phasing summation section
165: wave detection section
166: log compression section
167: dynamic range adjustment section
168: image plotting section
200: catheter
210: catheter body
240: signal line

The invention claimed is:

1. A guide wire comprising:
a guide wire body; and
a medical ultrasonic sensor array positioned at a distal end part of the guide wire body, the medical ultrasonic sensor array comprising a plurality of ultrasonic sensors having a plurality of first electrode plates, a plurality of piezoelectric elements, and a second electrode plate, wherein
each of the ultrasonic sensors has a respective one of the first electrode plates and a respective one of the piezoelectric elements sandwiched between the second electrode plate and the respective one of the first electrode plates,
each first electrode plate of each ultrasonic sensor is separated from each other first electrode plate of each other ultrasonic sensor,
the second electrode plate is a single body electrode plate shared by the plurality of the ultrasonic sensors,
the second electrode plate includes a plurality of cavities,
each cavity extends in a direction of thickness of the medical ultrasonic sensor array,
each cavity is formed in a surface of the second electrode plate at which the piezoelectric elements connect to the second electrode plate at a position between connection regions connecting a respective pair of the piezoelectric elements to the second electrode plate, the medical ultrasonic sensor array is positioned such that an ultrasonic sender-receiver face of the first electrode plate of each of the ultrasonic sensors faces in a direction of insertion of the guide wire body, and the medical ultrasonic sensor array is positioned further distal than a metallic core shaft of the guide wire.

2. The guide wire according to claim 1, wherein the second electrode plate of the medical ultrasonic sensor array is electrically connected to the core shaft.

3. The guide wire according to claim 2, further comprising an electrode terminal portion positioned at the proximal end part of the guide wire body; and a signal transmission portion that transmits a signal between the first electrode plates of each of the plurality of ultrasonic sensors and the electrode terminal portion, wherein the signal transmission portion comprises a plurality of signal lines, each signal line being disposed for a respective one of the plurality of ultrasonic sensors, and each signal line transmits a sent electric signal to be input to the respective ultrasonic sensor for sending ultrasound, from the electrode terminal portion to the respective ultrasonic sensor, and also transmits a received electric signal output from the respective ultrasonic sensor corresponding to received ultrasound, from the respective ultrasonic sensor to the electrode terminal portion.

\* \* \* \* \*